(12) United States Patent
Greco et al.

(10) Patent No.: US 10,772,911 B2
(45) Date of Patent: Sep. 15, 2020

(54) CELL FREE COMPOSITIONS FOR CELLULAR RESTORATION AND METHODS OF MAKING AND USING SAME

(71) Applicant: Advanced ReGen Medical Technologies, LLC, Houston, TX (US)

(72) Inventors: Steven John Greco, Houston, TX (US); Vincent C. Giampapa, Houston, TX (US)

(73) Assignee: Advanced ReGen Medical Technologies, LLC, Houston, TX (US)

( * ) Notice: Subject to any disclaimer, the term of this patent is extended or adjusted under 35 U.S.C. 154(b) by 0 days.

(21) Appl. No.: 15/128,660

(22) PCT Filed: Mar. 24, 2015

(86) PCT No.: PCT/US2015/022285
§ 371 (c)(1),
(2) Date: Sep. 23, 2016

(87) PCT Pub. No.: WO2015/148534
PCT Pub. Date: Oct. 1, 2015

(65) Prior Publication Data
US 2017/0173076 A1     Jun. 22, 2017

Related U.S. Application Data

(63) Continuation-in-part of application No. 14/577,978, filed on Dec. 19, 2014, now abandoned, which is a continuation-in-part of application No. PCT/US2014/071667, filed on Dec. 19, 2014.

(60) Provisional application No. 61/696,694, filed on Mar. 24, 2014, provisional application No. 61/919,165, filed on Dec. 20, 2013.

(51) Int. Cl.
| | |
|---|---|
| A61K 35/12 | (2015.01) |
| A61K 45/06 | (2006.01) |
| A61K 38/18 | (2006.01) |
| A61K 38/19 | (2006.01) |
| A61K 38/22 | (2006.01) |
| A61K 31/7105 | (2006.01) |
| A61K 35/15 | (2015.01) |

(52) U.S. Cl.
CPC .......... *A61K 35/12* (2013.01); *A61K 31/7105* (2013.01); *A61K 35/15* (2013.01); *A61K 38/18* (2013.01); *A61K 38/19* (2013.01); *A61K 38/22* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 2,984,164 | A | 5/1961 | Melle |
| 3,083,939 | A | 4/1963 | Gallagher, Jr. |
| 3,122,333 | A | 2/1964 | Steele et al. |
| 3,436,081 | A | 4/1969 | Ungar |
| 8,257,973 | B2 | 9/2012 | Park et al. |
| 8,747,915 | B1 | 6/2014 | Giampapa |
| 8,945,558 | B2 | 2/2015 | Kobara |
| 9,828,603 | B2 | 11/2017 | Marbán et al. |
| 9,994,814 | B2 | 6/2018 | Giampapa |
| 2004/0199935 | A1 | 10/2004 | Chapman |
| 2005/0158285 | A1 | 7/2005 | Giampapa |
| 2006/0188986 | A1 | 8/2006 | Millar et al. |
| 2007/0025973 | A1 | 2/2007 | Fitzsimmons et al. |
| 2007/0196918 | A1 | 8/2007 | Sayre et al. |
| 2008/0213812 | A1 | 9/2008 | Andrews et al. |
| 2008/0260704 | A1 | 10/2008 | Riordan et al. |
| 2008/0268429 | A1 | 10/2008 | Pietrzkowski |
| 2009/0011004 | A1 | 1/2009 | Lutz et al. |
| 2009/0317369 | A1 | 12/2009 | Hosoda et al. |
| 2009/0318345 | A1* | 12/2009 | Fibbe .................. A61K 38/193 514/1.1 |
| 2011/0003008 | A1 | 1/2011 | Lim |
| 2011/0177054 | A1 | 7/2011 | Gibbings et al. |
| 2011/0258716 | A1 | 10/2011 | Baltimore et al. |
| 2011/0300112 | A1 | 12/2011 | Marbán et al. |
| 2012/0093885 | A1 | 4/2012 | Sahoo et al. |
| 2012/0253102 | A1 | 10/2012 | Márban et al. |

(Continued)

FOREIGN PATENT DOCUMENTS

| | | |
|---|---|---|
| CA | 2845280 | 2/2012 |
| CN | 109475645 A | 3/2019 |

(Continued)

OTHER PUBLICATIONS

Foreign communication from a related counterpart application—European Search Report, European Patent Application No. 14571789, dated Feb. 12, 2018, 7 pages.

Foreign communication from a related counterpart application—Official Action, Japanese Patent Application No. 2016-0560872, dated Dec. 19, 2017, with translation, 14 pages.

Kim, Mi Jung, et al., "Age-related Deterioration of Hematopoietic Stem Cells," International Journal of Stem Cells, 2008, pp. 55-63, vol. 1, No. 1.

Archundia, A., et al., "Direct cardiac injection of G-CSF mobilized bone-marrow stem-cells improves ventricular function in old myocardial infarction," Life Sciences, Apr. 21, 2005, pp. 279-283, vol. 78, Elsevier Inc.

(Continued)

*Primary Examiner* — Blaine Lankford
(74) *Attorney, Agent, or Firm* — Knobbe, Martens, Olson & Bear, LLP

(57) ABSTRACT

A pharmaceutical formulation comprising exosomes derived from mobilized stem cells, and one or more pharmaceutically acceptable carriers, adjuvants, or vehicles. A pharmaceutical formulation comprising a microvesicles derived from mobilized stem cells, and one or more pharmaceutically acceptable carriers, adjuvants, or vehicles. A pharmaceutical formulation comprising an exosome-derived and/or microvesicle derived molecule and one or more pharmaceutically acceptable carriers, adjuvants, or vehicles.

5 Claims, 16 Drawing Sheets

(56) References Cited

U.S. PATENT DOCUMENTS

| | | |
|---|---|---|
| 2012/0258093 A1 | 10/2012 | Butler-Browne et al. |
| 2012/0321723 A1 | 12/2012 | Bruno et al. |
| 2013/0017176 A1 | 1/2013 | Hosoda et al. |
| 2013/0177593 A1 | 7/2013 | Gunn et al. |
| 2013/0195899 A1 | 8/2013 | Ichim et al. |
| 2013/0209528 A1* | 8/2013 | Levi ............... A61K 8/14 424/400 |
| 2013/0236428 A1 | 9/2013 | Giampapa |
| 2013/0302285 A1 | 11/2013 | Fong et al. |
| 2013/0336935 A1 | 12/2013 | Niedernhofer et al. |
| 2014/0004601 A1* | 1/2014 | Lim ............... C12N 5/0663 435/317.1 |
| 2014/0031256 A1 | 1/2014 | Lim |
| 2014/0088006 A1* | 3/2014 | Tsyrlova ............... A61K 38/10 514/6.9 |
| 2014/0120066 A1 | 5/2014 | Yeghiazarians et al. |
| 2014/0121171 A1 | 5/2014 | Muñoz-Cánoves et al. |
| 2014/0127284 A1 | 5/2014 | Cheresh |
| 2015/0023935 A1 | 1/2015 | Giampapa |
| 2015/0174166 A1 | 6/2015 | Giampapa |
| 2015/0203844 A1 | 7/2015 | Marbán et al. |
| 2015/0273113 A1 | 10/2015 | Marbán et al. |
| 2015/0328263 A1 | 11/2015 | Kaushal |
| 2016/0108370 A1 | 4/2016 | Greco et al. |
| 2016/0145571 A1 | 5/2016 | Giampapa |
| 2017/0087087 A1 | 3/2017 | Leonard et al. |
| 2017/0107581 A1 | 4/2017 | Kawauchi et al. |
| 2017/0173076 A1 | 6/2017 | Greco et al. |
| 2017/0275699 A1 | 9/2017 | Kawauchi et al. |
| 2017/0290860 A1 | 10/2017 | Marbán et al. |
| 2017/0304368 A1 | 10/2017 | Marbán et al. |
| 2017/0314019 A1 | 11/2017 | Greco et al. |
| 2018/0100149 A1 | 4/2018 | Marbán et al. |
| 2018/0360878 A1 | 12/2018 | Giampapa |
| 2018/0371465 A1 | 12/2018 | Hinkle |
| 2019/0000888 A1 | 1/2019 | Marbán et al. |

FOREIGN PATENT DOCUMENTS

| | | |
|---|---|---|
| EP | 2 687 219 | 1/2014 |
| EP | 2 823 039 | 1/2015 |
| EP | 2 984 164 | 2/2016 |
| EP | 3 122 333 | 2/2017 |
| EP | 3 436 081 | 2/2019 |
| JP | 2017510582 A | 4/2017 |
| JP | 6353073 B2 | 7/2018 |
| JP | 6471302 B2 | 2/2019 |
| KR | 10-2008-0049917 | 6/2008 |
| KR | 20170139701 A | 5/2017 |
| TW | 201739458 A | 11/2017 |
| WO | WO 2004/048555 | 6/2004 |
| WO | WO 2006/007529 | 1/2006 |
| WO | WO 2006/052925 | 5/2006 |
| WO | WO 2007/016245 | 2/2007 |
| WO | WO 2007/109223 | 9/2007 |
| WO | WO 2008/066330 | 6/2008 |
| WO | WO 2008/103135 A2 | 8/2008 |
| WO | WO 2009/086425 | 7/2009 |
| WO | WO 2009/105044 | 8/2009 |
| WO | WO 2011/029903 | 3/2011 |
| WO | WO 2012/020307 | 2/2012 |
| WO | WO 2012/149557 | 11/2012 |
| WO | WO 2012/162741 | 12/2012 |
| WO | WO 2013/048734 | 4/2013 |
| WO | 2013066368 | 5/2013 |
| WO | WO 2013/134513 | 9/2013 |
| WO | WO 2013/170170 | 11/2013 |
| WO | WO 2014/013258 | 1/2014 |
| WO | 2014028493 A2 | 2/2014 |
| WO | 2014028493 A3 | 2/2014 |
| WO | WO 2014/169077 | 10/2014 |
| WO | WO 2015/052527 | 4/2015 |
| WO | WO 2015/073625 | 5/2015 |
| WO | WO 2015/085096 | 6/2015 |
| WO | WO2015095794 A1 | 6/2015 |
| WO | WO 2015/120150 | 8/2015 |
| WO | WO 2015/148534 | 10/2015 |
| WO | WO 2015/182781 A1 | 12/2015 |
| WO | WO 2015/190542 A1 | 12/2015 |
| WO | WO 2016/054591 | 4/2016 |
| WO | WO 2016/057560 | 4/2016 |
| WO | WO 2017/190000 | 4/2017 |
| WO | WO 2009/011546 | 1/2019 |
| WO | WO 2019/028223 | 2/2019 |

OTHER PUBLICATIONS

Extended Search Report from a related European counterpart application, EP14871789.5, dated Apr. 13, 2017, 7 pages.

Baglio, S. R., et al,. "Mesenchymal stem cell secreted vesicles provide novel opportunities in (stem) cell-free therapy," Friontiers in Physiology, Sep. 6, 2012, pp. 1-11, vol. 3.

Kordelas, L., et al., "MSC-derived exosomes: a novel tool to treat therapy-refractory graft-versus-host disease," Leukemia, Jan. 21, 2014, pp. 970-973, vol. 28, Macmillan Publishers Limited.

Yu, B., et al., "Exosomes Derived from Mesenchymal Stem Cells," International Journal of Molecular Sciences, Mar. 7, 2014, pp. 4142-4157, vol. 15.

Iglesias, D. M., "Stem Cell Microvesicles Transfer Cystinosin to Human Cystinotic Cells and Reduce Cystine Accumulation in Vitro," PLOS ONE, Aug. 13, 2012, pp. 1-9, vol. 7, No. 8.

International Search Report and Written Opinion for PCT Application No. PCT/US2015/022285, dated Jun. 30, 2015.

International Search Report and Written Opinion for PCT Application No. PCT/US2014/071667, dated Mar. 31, 2015.

Mittelbrunn, Maria et al., "Unidirectional transfer of microRNA-loaded exosomes from T cell to antigen-presenting cells", Nature Communications, 2011, vol. 2, Article No. 282.

Li, Shu-Hong et al., "Reconstitution of aged bone marrow with young cells repopulates cardiac-resident bone marrow derived progenitor cells and prevents cardiac dysfunction after a myocardial infarction", European Heart Journal, Apr. 16, 2012, vol. 34, No. 15.

Melamed, Doron et al., "Aging and neoteny in the B lineage", Blood, 2012, vol. 120, No. 20.

Shen, Jinhui et al., "Transplantation of mesenchymal stem cells from young donors delays aging in mice", Scientific Reports, 2011, vol. 1, Article No. 67.

Filing Receipt and Specification for provisional application entitled "Stem Cell Compositions and Methods of Using Same," by Vincent C. Giampapa, filed Dec. 20, 2013 as U.S. Appl. No. 61/919,165.

Office Action dated Sep. 21, 2017 (10 pages), U.S. Appl. No. 14/577,978 filed, Dec. 19, 2014.

Foreign communication from a related counterpart application—European Examination Report, European Patent Application No. 15768892.0, dated Nov. 6, 2018, 7 pages.

Mildner, Michael, et al., "Secretome of Peripheral Blood Mononuclear Cells Enhances Wound Healing," PLoS ONE, Mar. 22, 2013, pp. 1-8, vol. 8, No. 3.

Hoetzenecker, Konrad, et al., "Mononuclear cell secretome protects from experimental autoimmune myocarditis," European Heart Journal, Jan. 15, 2013, pp. 676-685, vol. 36, No. 11.

Kroschinsky, Frank, et al., "Single-dose pegfilgrastim for the mobilization of allogeneic CD34+ peripheral blood progenitor cells in healthy family and unrelated donors," Haematologica, Dec. 1, 2005, pp. 1665-1671, vol. 90, vol. 12, Ferrata Storti Foundation.

Beelen, Dietrich W., et al., "Transplantation of Filgrastim-Mobilized Peripheral Blood Stem Cells From HLA-Identical Sibling or Alternative Family Donors in Patients With Hematologic Malignancies: A Prospective Comparison on Clinical Outcome, Immune Reconstitution, and Hematopoietic Chimerism," Blood, Dec. 15, 1997, pp. 4725-4735, vol. 90 vol. 12, The American Society of Hematology.

Final Office Action dated Apr. 17, 2018 (20 pages), U.S. Appl. No. 14/577,978, filed Dec. 19, 2014.

Filing Receipt and Specification for divisional application entitled "Compositions for Cellular Restoration and Methods of Making and Using Same," filed Aug. 24, 2018 as U.S. Appl. No. 16/111,832.

(56) References Cited

OTHER PUBLICATIONS

Advisory Action dated Jul. 12, 2018 (2 pages), U.S. Appl. No. 14/577,978, filed Dec. 19, 2014.
Ajijola et al., "Ventricular Tachycardia in Ischemic Heart Disease Substrates", Indian Heart Journal, 2014, pp. S24-S34, S28 & S30, vol. 66, Supplement 1.
Aminzadeh et al., "Heart-Derived Cell Therapy for Duchenne Cardiomyopathy: Cardiosphere-Derived Cells and their Exosomes Improve Function, Restore Mitochondrial Integrity and Reverse Degenerative Changes in the Hearts of Mdx Mice", Circulation Research, Dec. 5, 2014, vol. 115, No. 12, 24248, pp. E90-E91.
Chen et al., "Mesenchymal Stem Cell Secretes Microparticles Enriched in Pre-MicroRNAs", Nucleic Acids Research, 2010, vol. 38, No. 1, pp. 215-224.
Chimenti et al., "Relative Roles of Direct Regeneration Versus Paracrine Effects of Human Cardiosphere-Derived Cells Transplanted Into Infarcted Mice", Circulation Research, Mar. 19, 2010, vol. 106, pp. 971-980.
Conboy, Irina M. et al, "Rejuvenation of aged progenitor cells by exposure to a young systemic environment", Nature, vol. 433, No. 7027, Feb. 17, 2005, pp. 760-764.
De Bakker et al, "Slow Conduction in the Infarcted Human Heart 'Zigzag' Course of Activation", Circulation, Sep. 1993, pp. 915-926, vol. 88, No. 3.
De Couto et al., "Macrophages Mediate Cardioprotective Cellular Postconditioning in Acute Myocardial Infarction", The Journal of Clinical Investigation, Jul. 27, 2015, vol. 125, No. 8, pp. 3147-3162.
Foreign communication from a related counterpart application—Extended European Search Report, European Patent Application No. 15768892, dated Oct. 26, 2017, 9 pages.
Grigorian-Shamagian et al., "Cardiac and Systemic Rejuvenation After Cardiosphere-Derived Cell Therapy in Senescent Rats", European Heart Journal, Oct. 14, 2017, vol. 38, No. 39, pp. 2957-2967.
Guan, X, et al., "miR-223 regulates adipogenic and osteogenic differentiation of mesenchymal stem cells through a CI EBPs/miR-223/FGFR2 regulatory feedback loop," Stem Cells, 2015, pp. 1589-1600, vol. 33, AlphaMed Press.
Halley-Stott, Richard P., et al., "Nuclear reprogramming," Development at a Glance, 2013, vol. 2468-2471, The Company of Biologists Ltd.
Hine et al., "NRF2 and the Phase II Response in Acute Stress Resistance Induced by Dietary Restriction", Journal of Clinical & Experimental Pathology, Jun. 19, 2012, vol. S4, No. 4, pp. 1-33.
Hsieh, J.-Y., et al., "miR-146a-5p circuitry uncouples cell proliferation and migration, but not differentiation, in human mesenchymal stem cells," Nucleic Acids Research, 2013, pp. 9753-9763, vol. 41, No. 21.
Hu et al., "MicroRNA-210 as a Novel Therapy for Treatment of Ischemic Heart Disease", Circulation, Sep. 14, 2010, vol. 122, Supplement 11, S124-S131, pp. 17.
Ibrahim et al., "Exosomes as Critical Agents of Cardiac Regeneration Triggered by Cell Therapy", Stem Cell Reports, May 6, 2014, vol. 2, pp. 606-619.
Ibrahim et al., "Microrna-Containing Exosomes from Cardiosphere-Derived Cells Stimulate Cardiomyocyte Proliferation and Angiogenesis in Vitro, and Improve Functional Recovery after Myocardial Infarction in Mice", Circulation, 2012, vol. 126, Abs. 14697, pp. 4.
Ibrahim et al., "Role of Exosomes and Their MicroRNA Constituents in Mediating the Therapeutic Benefits of Human Cardiosphere-Derived Cells in Vitro and in Mice with Myocardial Infarction", Circulation, Nov. 26, 2013, vol. 128, No. 22, Abs. 19186, pp. 2.
International Search Report and Written opinion for PCT Application No. PCT/US2015/022285, dated Jun. 30, 2015 10 pages.
Jayawardena et al., MicroRNA-Mediated in Vitro and in Vivo Direct Reprogramming of Cardiac Fibroblasts to Cardiomyocytes, Circulation Research, 2012, vol. 110, No. 11, pp. 1465-1473.
Kamdar et al., "Dystrophin-Deficient Cardiomyopathy", Journal of the American College of Cardiology, 2016, vol. 67, No. 21, pp. 2533-2546.

Kooijmans et al., "PEGylated and Targeted Extracellular Vesicles Display Enhanced Cell Specificity and Circulation Time", Journal of Controlled Release, 2016, vol. 224, pp. 77-85.
Lai et al., "Exosome Secreted by MSC Reduces Myocardial Ischemia/Reperfusion Injury", Stem Cell Research, 2010, vol. 4, pp. 214-222.
Lavasani, Mitra, et al., "Muscle-derived stem/ progenitor cell dysfunction limits healthspan and lifespan in a murine progeria model," Nature Communications, Jan. 3, 2012, pp. 1-12, vol. 3, No. 608, Macmillan Publishers Limited.
Lee et al., "Intramyocardial Injection of Autologous Cardiospheres or Cardiosphere-Derived Cells Preserves Function and Minimizes Adverse Ventricular Remodeling in Pigs With Heart Failure Post-Myocardial Infarction", Journal of the American College of Cardiology, Jan. 25, 2011, vol. 57, No. 4, pp. 455-465.
Li et al., "Direct Comparison of Different Stem Cell Types and Subpopulations Reveals Superior Paracrine Potency and Myocardial Repair Efficacy with Cardiosphere-Derived Cells", Journal of American College of Cardiology, 2012, vol. 59, No. 10, pp. 942-953.
McCullagh, Karl J A: "Can a young muscle's stem cell secretome prolong our lives?", Stem Cell Research & Therapy, vol. 3, May 2012.
Melief, Sara et al., "Multipotent stromal cells skew monocytes towards an anti-inflammatory interleukin-10-producing phenotype by production of interleukin-6," Haematologica, Jan. 24, 2013, 98(6): pp. 888-895.
Middleton et al., "Newt Cells Secrete Extracellular Vesicles with Therapeutic Bioactivity in Mammalian Cardiomyocytes", Journal of Extracellular Vesicles, 2018, vol. 7, pp. 1-15.
Ousaka et al., "Abstract 13881: Cardiac Progenitor Cell Infusion in Patients With Univentricular Heart Diseases in Heart Failure With Preserved Ejection Fraction", Circulation, Abstract 13881, 2015, vol. 132, <http://circ.ahajournals.org/content/132/Suppl_3/A13881.short>.
Ple et al., "The Repertoire and Features of Human Platelet microRNAs,"(PLOS One (2012) vol. 7(12), article# e507 46, 14 pages). (Year: 2012).
Rando, Thomas A., et al., "Aging, Rjuvenation, and Epigenetic Reprogramming: Resetting the Aging Clock," Cell, Jan. 20, 2012, vol. 148, pp. 46-57, Elsevier Inc.
Ratajczak M Z et al: "Pivotal role of paracrine effects in stem cell therapies in regenerative medicine: can we translate stem cell-secreted paracrine factors and microvesicles into better therapeutic strategies?", Leukemia (Basingstoke), vol. 26, No. 6, Jun. 2012.
Rathore (2011, Preparative Biochemistry and Biotechnology, 41 :398-421).
Reiffel, James A., MD, FACC, "Ten Pearls for the Use of Antiarrhythmic Drugs for Atrial Fibrillation", Aug. 17, 2012, Retrieved from <http://www.acc.org/latest-in-cardiology/articles/2014/07/18/15/12/ten-pearls-for-the-use-of-antiarrhythmic-drugs-for-atrial-fibrillation>, pp. 17.
Scaria et al., "Host-Virus Genome Interactions: Marco Roles for MicroRNAs", Cellular Microbiology, 2007, vol. 9, No. 12, pp. 2784-2794.
Sharma et al., "Cardiosphere Derived Cells from Pediatric End-Stage Heart Failure Patients Have Enhanced Functional Activity due to the Heat Shock Response Regulating the Secretome", Stem Cells, Apr. 2015, pp. 1213-1229, vol. 33, No. 4.
Shmazaki, T., et al., "Heterochronic microRNAs in temporal specification of neural stem cells: application toward rejuvenation," NPJ Aging and Mechanisms of Disease, Jan. 7, 2016, pp. 1-6, vol. 2, No. 15014, Japanese Society of Anti-Aging Medicine/Macmillan Publishers Limited.
Simonsson, Stina, et al., "DNA demethylation is necessary for the epigenetic reprogramming of somatic cell nuclei," Nature Cell Biology, Oct. 2004, vol. 6, No. 10, pp. 984-990, Nature Publishing Group.
Singhal, Nishant, et al., "Chromatin-Remodeling Components of the BAF Complex Facilitate Reprogramming," Cell, Jun. 11, 2010, vol. 141, pp. 943-955, Elsevier Inc.

(56) References Cited

OTHER PUBLICATIONS

Sun, Yun, et al., "Rescuing replication and osteogenesis of aged mesenchymal stem cells by exposure to a young extracellular matrix," The FASB Journal, May 2011, vol. 25, No. 5, pp. 1474-1485.
Tatsumi, Kimiko et al: "Granulocyte-Colony Stimulation Factor Increases Donor Mesenchymal Stem Cells in Bone Marrow and Their Mobilization Into Peripheral Circulation but Does Not Repair Dystrophic Heart After Bone Marrow Transplantation", Cire J, 2008 ; 72: 1351-1358.
Tseliou et al., "Allogeneic Cardiospheres Safely Boost Cardiac Function and Attenuate Adverse Remodeling After Myocardial Infarction in Immunologically Mismatched Rat Strains", Journal of the American College of Cardiology, Mar. 12, 2013, vol. 61, No. 10, pp. 1108-1119.
U.S. Appl. No. 13/785,691, filed Mar. 5, 2013 including prosecution history.
U.S. Appl. No. 14/509,523, filed Oct. 8, 2014 including prosecution history.
U.S. Appl. No. 14/577,978, filed Dec. 19, 2014 including prosecution history.
U.S. Appl. No. 14/889,942, filed Nov. 9, 2015 including prosecution history.
U.S. Appl. No. 14/922,353, filed Oct. 26, 2015 including prosecution history.
U.S. Appl. No. 15/581,705, filed Apr. 28, 2017 including prosecution history.
U.S. Appl. No. 16/111,832, filed Aug. 24, 2018 including prosecution history.
U.S. Appl. No. 16/250,940, filed Jun. 17, 2019 including prosecution history.
Vrijsen et al., "Cardiomyocyte Progenitor Cell-Derived Exosomes Stimulate Migration of Endothelial Cells", Journal of Cellular and Molecular Medicine, 2010, vol. 14, No. 5, pp. 1064-1070.
Ibrahim, A., et al. "Exosomes: Fundamental Biology and Roles in Cardiovascular Physiology," Annu. Rev. Physiol., 78, 68-83, 2017.
Baker, Darren J. et al., "Clearance of p16Ink4a-positive senescent cells delays ageing-associated disorders" Nature, Nov. 1, 2011, vol. 479, No. 7372, pp. 232-236.
Bougel, S. et al., 'PAX5 activates the transcription of the human telomerase reverse transcriptase gene in B cells', J. Pathol. 2010, vol. 220, No. 1, pp. 87-96.
He, X. et al., "Human Fibroblast Reprogramming to Pluripotent Stem Cells Regulated by the miR19a/b-PTEN Axis" PLOS One, Apr. 16, 2014, vol. 9, No. 4, p. e95213.
Jurmeister, S. et. al., 'MicroRNA-200c represses migration and invasion of breast cancer cells by targeting actin-regulatory proteins FHOD1 and PPM1F', Mol. Cell. Biol., Feb. 2012, vol. 32, No. 3, pp. 633-651.
Lam et al. (Molecular Therapy—Nucleic Acids (2015) vol. 4: pp. 1-20).
Li, Zhonghan et al, "Small RNA-mediated regulation of iPS cell generation", EMBO Journal, Feb. 1, 2011, vol. 30, pp. 823-834.
Liang, J., et al., "MicroRNA-103a inhibits gastric cancer cell proliferation, migration and invasion by targeting c-Myb" Cell Proliferation, Dec. 22, 2014, vol. 48, No. 1, pp. 78-85.
Lu, D., et al., 'The miR-155-PU.1 axis acts on Pax5 to enable efficient terminal B cell differentiation', J. Exp. Med., 2014, vol. 211, No. 11, pp. 2183-2198.

NCBI Reference Sequence No. NM.014634.3, 'Homo sapiens protein phosphatase, Mg2+/Mn2+ dependent 1F (PPM1F), mRNA', Oct. 16, 2017.
NCBI Reference Sequence No. NM_016734.2, 'Homo sapiens paired box 5 (PAX5), transcript variant 1, mRNA', Nov. 30, 2017.
NCBI Reference Sequence No. NR_030350.1, 'Homo sapiens microRNA 619 (MIR619), microRNA', Jun. 26, 2017.
PPM 1 F Wikipedia downloaded from https ://en. wikipedia .org/wiki/P PM 1 F on Sep. 9, 2019.
Suh, Mi-Ra, et al., "Human embryonic stem cells express a unique set of mircoRNAs" Development Biology, May 6, 2004, vol. 270, No. 2, pp. 488-498.
Sugihara et al., "Carnosine induces intestinal cells to secrete exosomes that activate neuronal cells." PLOS ONE (2019) 14(5)e:0217394; pp. 1-17.
Tu, S.H. et al., 'Protein phosphatase Mg2+/Mn2+ dependent 1F promotes smoking-induced breast cancer by inactivating phosphorylated-p53-induced signals', Oncotarget, Oct. 18, 2016, vol. 7, No. 47, pp. 77516-77531.
Yu, Bin et al., "Exosomes secreted from GATA-4 overexpressing mesenchymal stem calls serve as a reservoir of anti-apoptotic microRNAs for cardioprotection" International Journal of Cardiology, Dec. 23, 2014, vol. 182, pp. 349-360.
Yu, Ge et al., "MicroRNA-19a targets tissue factor to inhibit colon cancer cells migration and invasion" Molecular and Cellular Biochemistry, May 12, 2013, vol. 380, No. 1-2, pp. 239-247.
Rejenevie Therapeutics [rejenevie]. (published on May 15, 2019). "The Science Behind Immune Restoration," [Video file]. Retrieved from https://youtu.be/alKFhloo-L4, (transcript provided herewith).
Rejenevie Therapeutics [rejenevie]. (published Jun. 10, 2019). "10 Steps to Immune Restoration with Rejenevie," [Video file]. Retrieved from https://youtu.be/ulCaTgjXXf8, (transcript provided herewith).
Rejenevie Therapeutics [rejenevie]. (published May 10, 2019). "FAQs for Patients: Restoration & Young Donors," [Video file]. Retrieved from https://youtu.be/GOm_Q5nTbPM, (transcript provided herewith).
Rejenevie Therapeutics [rejenevie]. (published May 10, 2019). "FAQs for Patients: Okyanos & Post-Treatment Testing," [Video file]. Retrieved from https://youtu.be/YU-v4yic36I, (transcript provided herewith).
Rejenevie Therapeutics [rejenevie]. (published May 10, 2019). "FAQs for Patients: Screening, Mobilization & Treatment," [Video file]. Retrieved from https://youtu.be/V3NIJ-emB1U, (transcript provided herewith).
Rejenevie Therapeutics [rejenevie]. (published on May 23, 2019). "The Science Behind the Transwell System," [Video file]. Retrieved from https://youtu.be/Y75UXv747IQ, (transcript provided herewith).
R Y Niyazova et al: "The interaction of miRNAs with mRNAs of the cell cycle genes in lung cancer", Proceedings of the Moscow Conference on Computational Molecular Biology (MCCMB'15), Jul. 2015, XP55595996.
Shi-Jie Zhang et al: "miR-1303 Targets Claudin-18 Gene to Modulate Proliferation and Invasion of Gastric Cancer Cells", Digestive Diseases and Sciences, vol. 59, No. 8, Mar. 20, 2014, pp. 1754-1763, XP55595270.
Foreign communication from a related counterpart application—Canadian Office Action, Canadian patent Application No. 3023468, dated Aug. 27, 2019.

* cited by examiner

CELL FREE COMPOSITIONS FOR CELLULAR RESTORATION AND METHODS OF MAKING AND USING SAME

TECHNICAL FIELD

The present disclosure generally relates to compositions and methodologies for the improvement and/or restoration of one or more aspects of cellular function. More specifically this disclosure relates to compositions comprising isolated restoring elements.

BACKGROUND

Aging is an important risk factor for most chronic diseases and is the primary factor for the majority of morbidity and health care expenditures in developed nations. Decreased cellular function associated with cellular senescence results in the disorders and dysfunctions typically associated with aging mammalian cells. A potent inducer of cellular senescence is (epi)genomic stress, which can result from direct DNA damage, dysfunctional telomeres, disrupted chromatin, or strong mitogenic signals. Additionally, cellular senescence can cause chronic inflammation mediated, at least in part, by senescence-associated secretory factors (SASF).

There exists an ongoing need for compositions and methods that improve cellular functions that have been negatively impacted due to one or more mechanisms associated with cellular senescence. Further, there exists an ongoing need for compositions and methods to improve the cellular health of a subject.

SUMMARY

Disclosed herein is a pharmaceutical formulation comprising exosomes derived from mobilized stem cells, and one or more pharmaceutically acceptable carriers, adjuvants, or vehicles.

Also disclosed herein is a pharmaceutical formulation comprising a microvesicles derived from mobilized stem cells, and one or more pharmaceutically acceptable carriers, adjuvants, or vehicles.

Also disclosed herein is a pharmaceutical formulation comprising an exosome-derived and/or microvesicle derived molecule and one or more pharmaceutically acceptable carriers, adjuvants, or vehicles.

BRIEF DESCRIPTION OF THE DRAWINGS

For a more complete understanding of the present disclosure and the advantages thereof, reference is now made to the following brief description, taken in connection with the accompanying drawings and detailed description, wherein like reference numerals represent like parts.

DETAILED DESCRIPTION

Figure 1:
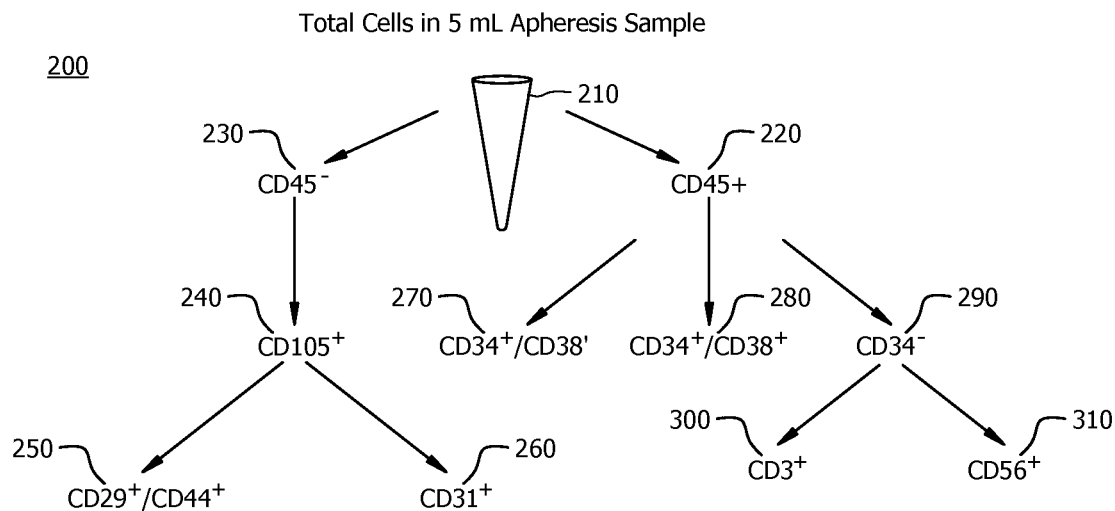
FIG. 1 is a depiction of an embodiment for immunophenotyping a cell sample.

Disclosed herein are compositions and methods for improving and/or restoring one or more cellular functions. These cellular functions may be directly or indirectly associated with promoting cellular health in a subject. Herein the term "promoting cellular health" refers to alterations in parameters of cellular function that result in a perceived and/or quantifiable improvement in the viability state of cells and/or cell types. The viability state of a cell may be assessed using any suitable metric to evaluate parameters such as, but not limited to, cellular architecture, membrane organization and/or integrity, dynamic protein assemblies, molecular organization, and cellular responses to external signals. The compositions and methods disclosed herein may improve the viability state of a cell as assessed by any suitable methodology. In an embodiment, a subject having improved and/or restored cellular function via the compositions and/or methodologies disclosed herein exhibits a perceived and/or quantifiable improvement in one or more aspects of the subject's cellular and/or general health.

The term "subject" as used herein, refers to an animal which is the object of treatment, observation, or experiment. By way of example only, a subject may be, but is not limited to, a mammal including, but not limited to, a human. The terms "treat," "treating," or "treatment," as used herein, include alleviating, abating, or ameliorating a disease or condition, or symptoms thereof; managing a disease or condition, or symptoms thereof; preventing additional symptoms; ameliorating or preventing the underlying metabolic causes of symptoms; inhibiting the disease or condition, e.g., arresting the development of the disease or condition; relieving the disease or condition; causing regression of the disease or condition; relieving a condition caused by the disease or condition; and/or stopping the symptoms of the disease or condition. The terms "treat," "treating," or "treatment," include, but are not limited to, prophylactic and/or therapeutic treatments. "Prophylactic treatment" or "therapeutic treatment" refers to administration to the subject of one or more of the disclosed compositions. If it is administered prior to clinical manifestation of an unwanted condition (e.g., medical condition, disease, disorder, dysfunction) then the treatment is prophylactic, i.e., it protects the subject against developing the unwanted condition, whereas if administered after manifestation of the unwanted condition, the treatment is therapeutic (i.e., it is intended to diminish, ameliorate, or maintain the existing unwanted condition or side effects therefrom). It is contemplated that a subject prophylactically treated for a medical condition with the compositions and methodologies disclosed herein may nonetheless develop said medical condition; however, prophylactic treatment may be beneficial in terms of lessening the severity and/or duration of the medical condition. Treatment as used herein also encompasses any pharmaceutical or medicinal use of the compositions herein.

In an embodiment, the subject is administered the compositions disclosed herein in a therapeutically effective amount sufficient for treating, preventing, and/or ameliorating one or more symptoms of a medical condition, disorder, disease, or dysfunction. Hereinafter, for simplicity, the unwanted condition which has been used interchangeably with the terms medical condition, disorder, disease, and dysfunction are collectively referred to as the "medical condition." As used herein, amelioration of the symptoms of the medical condition by administration of a particular composition of the type disclosed herein refers to any lessening, whether lasting or transient, which can be attributed to or associated with administration of compositions of the type disclosed herein. As used herein, a "therapeutically effective amount" means a sufficient amount of the compositions disclosed herein to treat, prevent, and/or ameliorate one or more symptoms of the medical condition. It also may include a safe and tolerable amount of the compositions disclosed herein, as based on industry and/or regulatory standards. As will be understood by the ordinarily skilled artisan an amount that proves to be a "therapeutically effective amount" in a given instance, for a particular subject, may not be effective for 100% of subjects similarly treated for the medical condition under consideration, even though such dosage is deemed a "therapeutically effective amount" by ordinarily skilled practitioners. The therapeutically effective amount for a particular individual may vary depending on numerous factors such as the nature of the medical condition, severity of the medical condition, subject weight, subject age, and the general health of the subject. It is contemplated that the therapeutically effective amount may be optimized by one or more healthcare professionals in consideration of the particular factors affecting a subject.

One or more compositions disclosed herein may comprise cells and/or cellular material obtained from a human subject. Herein the term "cellular material" refers to materials derived from, secreted by, and otherwise currently or previously associated with a cell.

In an embodiment, a method of the present disclosure comprises (i) obtaining a donor cell sample and a receiver cell sample; (ii) utilizing one or more analytical techniques to characterize the donor cell sample and receiver cell sample; (iii) contacting one or more components of the donor cell sample with the receiver cell sample to generate a restored cell sample; (iv) utilizing one or more analytical techniques to characterize the restored cell sample; and (v) utilizing the restored cell sample for treatment of a subject.

In an alternative embodiment, a method of the present disclosure comprises (i) obtaining a donor cell sample and a receiver cell sample; (ii) contacting one or more components of the donor cell sample with the receiver cell sample to generate a restored cell sample; and (iii) utilizing the restored cell sample for treatment of a subject.

In yet another embodiment, a method of the present disclosure comprises (i) obtaining a first cell sample from a first subject; (ii) obtaining a second cell sample from a second subject; (iii) culturing the first cell sample in the presence of at least a portion of a culture media of the second cell sample for a time period ranging from about 24 hours to about 6 weeks to produce a restoring composition; and (iv) contacting the restoring composition with the second cell sample for a period of time ranging from about 24 hours to about 6 weeks to produce a restored composition.

In an embodiment, the donor cell sample is provided by a donor subject while the receiver cell sample is provided by a receiver subject. In some embodiments, the donor subject and receiver subject are the same. Alternatively, the donor subject and receiver subject are different. In an embodiment, the donor subject is chosen such that the difference in the age of the donor subject, designated x, and the age of the receiver subject, designated y, is greater than about 5 years, alternatively, greater than about 10 years, alternatively greater than about 15 years, alternatively greater than about 20 years, alternatively greater than about 25 years, or alternatively greater than about 30 years where y is greater than x. In an embodiment, the donor subject is chosen such that the difference in the age of the donor subject, x, and the age of the receiver subject, y, is from about 5 years to about 75 years, alternatively from about 10 years to about 60 years, alternatively from about 15 years to about 50 years, alternatively from about 20 years to about 40 years, or alternatively from about 20 years to about 30 years where y is greater than x.

In some embodiments, the difference in chronological age between the donor subject and receiver subject is equal to or greater than about 16 years, alternatively from about 16 years to about 80 years, alternatively from about 16 years to about 50 years, or alternatively from about 16 years to about 30 years and x is greater than y. In yet another embodiment, the difference in chronological age between the donor subject and the receiver subject is less than about 365 days.

In an embodiment, the donor subject and receiver subject are related by consanguinity. Alternatively, the donor subject and receiver subject are not related. In an embodiment, the receiver subject has a medical condition that is absent from or undiagnosed in the donor subject. In either of the above disclosed embodiments, the donor subject and the receiver subject are adults, i.e., have reached sexual maturity. Alternatively, in either of the above disclosed embodiments, the donor subject has reached sexual maturity. Alternatively, in either of the above disclosed embodiments, the receiver subject has reached sexual maturity.

In an embodiment, the receiver subject is identified as having one or more risk factors associated with the development of a medical condition. In yet another embodiment, the receiver subject has not been diagnosed with a medical condition and/or has not been identified as having one or more risk factors associated with the development of a medical condition. It is contemplated that the methodologies disclosed herein may be employed in the treatment of subjects having a medical condition for which additional therapies have been previously or are currently being employed. It is further contemplated that in an embodiment, a receiver subject has undergone or is currently undergoing one or more therapies for medical conditions not associated with the medical condition for which the subject will be treated using the compositions and methodologies disclosed herein. In an embodiment, the receiver subject has one or more age-related medical conditions.

In an embodiment, the donor cell sample, receiver cell sample, or both are obtained from a subject(s) who has undergone a Stage B preparation. In some embodiments, the donor cell sample, receiver cell sample, or both are obtained from a subject(s) who has undergone a Stage A preparation and a Stage B preparation.

In an embodiment, the donor cell sample, the receiver cell sample, or both are obtained from a subject that has undergone a Stage A preparation. Herein, a Stage A preparation of a subject comprises the utilization of methods and/or compositions to improve the subject's general health prior to obtaining a composition (i.e., donor cell sample or receiver cell sample) from the subject.

A nonlimiting example of a methodology to improve the subject's general health includes the administration of one or more metabolic mediators to the subject. Herein, metabolic mediator refers to a substance which, when present in insufficient amounts in the subject, is detrimental to the physiological and/or psychological state of the subject or whose presence positively impacts the physiological and/or psychological state of the subject. The subject may be administered a plurality of metabolic mediators prior to obtaining one or more compositions of the type disclosed herein from the subject.

In an embodiment, the metabolic mediator comprises a nutraceutical. Herein, a nutraceutical refers to a material that may be derived from a natural source and that provides health benefits. A nonlimiting example of a nutraceutical suitable for use in the Stage A preparation of a subject is commercially available as EVERYCELL®, HEALTHYCELL, or HEALTHYCELL PLUS from Cell Health Institute. Additional compositions suitable for use metabolic mediators in the present disclosure are described in U.S. Pat. Nos. 8,747,915 and 8,974,839 entitled "Dietary Supplement System for Multifunctional Anti-Aging Management and Method of Use" which is incorporated by reference herein in its entirety.

Another example of a methodology suitable for use in Stage A preparation of a subject comprises the administration of one or more pulsed electromagnetic fields (PEMF) to at least a portion of the subject's body prior to and/or concurrent with, obtaining a sample of the type disclosed herein. PEMF may be used to enhance the homing, engraftment, and/or differentiation of the adult stem cells.

Stage A preparation of a subject may be carried out for some period of time prior to, and/or concurrent with obtaining a cell sample of the type disclosed herein from the subject. For example, Stage A preparation of a subject may comprise administration of a nutraceutical to the subject at a particular dosage (e.g., 500 mg, twice daily) for a period of time greater than about 48 hours prior to obtaining a cell sample of the type disclosed herein from the subject. Alternatively, the nutraceutical is administered for a time period of from about 48 hours to about 1 year prior to obtaining a cell sample of the type disclosed herein from the subject, alternatively from about 1 week to about 9 months, or alternatively from about 1 month to about 6 months. In some embodiments, the subject may be administered or may self-administer the nutraceutical for any period of time prior to, concurrent with, or subsequent to the procurement of a cell sample.

In an embodiment, the donor cell sample, the receiver cell sample, or both are obtained from a subject that has undergone a Stage B preparation. In an embodiment, during a Stage B preparation, the subject (donor and/or receiver) undergoes at least one process for mobilizing the subject's stem cells. Herein "stem cells" are given their usual meaning which generally refers to cells which are not terminally differentiated and are therefore able to produce cells of other types. Stem cells are typically divided into three types, including totipotent, pluripotent, and multipotent. "Totipotent stem cells" can grow and differentiate into any cell in the body, and thus can grow into an entire organism. These cells are not capable of self-renewal. In mammals, the zygote and early embryonic cells are totipotent. "Pluripotent stem cells" are true stem cells, with the potential to make any differentiated cell in the body, but cannot contribute to making the extraembryonic membranes (which are derived from the trophoblast). "Multipotent stem cells" are clonal cells that self-renew, as well as differentiate, to regenerate adult tissues. "Multipotent stem cells" are also referred to as "unipotent" and can only become particular types of cells, such as blood cells or bone cells.

In an embodiment, the donor and receiver cell samples comprise adult stem cells and/or adult stem cell material which refer to stem cells or stem cell material that are not embryonic in origin nor derived from embryos or fetal tissue. In an alternative embodiment, the donor cell sample comprises adult stem cells and/or adult stem cell material which refer to stem cells or stem cell material that are not embryonic in origin or derived from embryos or fetal tissue. In an embodiment, the donor and receiver cell samples comprise stem cells and/or stem cell material that are embryonic in origin and/or derived from embryos or fetal tissue. In an alternative embodiment, the donor cell sample comprises stem cells and/or stem cell material that are embryonic in origin and/or derived from embryos or fetal tissue.

In an embodiment, Stage B preparation comprises administering to a subject an effective amount of a mobilizer. Herein a "mobilizer" or a "mobilizer of hematopoietic stem cells or progenitor cells" (used interchangeably) refers to any substance, whether it is a small organic molecule, synthetic or naturally derived, or a polypeptide, such as a growth factor or colony-stimulating factor or an active fragment or mimic thereof, a nucleic acid, a carbohydrate, an antibody, or any other agent that acts to enhance the migration of stem cells from the bone marrow into the peripheral blood. Such a "mobilizer" may increase the number of stem cells (e.g., hematopoietic stem cells or hematopoietic progenitor/precursor cells) in the peripheral blood, thus allowing for a more accessible source of stem cells for use in the methods disclosed herein. Any mobilizer suitable for increasing the number of stem cells in the subject that are available to be harvested and is compatible with the other aspects of this disclosure may be utilized. In an embodiment, the mobilizer is a cytokine such as granulocyte colony-stimulating factor (G-CSF). A commercial example of a mobilizer suitable for use in the present disclosure is NEUPOGEN® (filgrastim) which is a prescription medication used to treat neutropenia that is commercially available from Amgen. Another example of a mobilizer suitable for use in the present disclosure is a recombinant methionyl human stem cell factor which is commercially available as STEMGEN® from Amgen. Yet another example of a mobilizer suitable for use in the present disclosure is plerixafor which is an inhibitor of the CXCR4 chemokine receptor and blocks binding of its cognate ligand, stromal cell-derived factor-1α (SCF-1α) and is commercially available as MOZOBIL® from Genzyme.

An effective amount of a mobilizer may be determined by the ordinarily skilled artisan consistent with best medical practices and taking into account a variety of factors including, for example and without limitation, the subject's general health and body mass.

As known to one of ordinary skill in the art, stem cells have been identified in various organs and tissues, including brain, bone marrow, peripheral blood, blood vessels, skeletal muscle, skin, teeth, heart, gut, liver, ovarian epithelium, and testis. It is contemplated that utilization of Stage B preparation of a subject would be carried out when obtaining stem cells using bone marrow as the source. It is within the scope of this disclosure to conduct various embodiments of the present methods using cell samples comprising stem cells obtained from any of the tissues known to be a source of stem cells. In such embodiments, Stage B preparation of the subject may not be carried out.

In an embodiment, a donor subject, a receiver subject, or both undergo Stage A preparation. In an embodiment, a donor subject, a receiver subject, or both undergo Stage B preparation. In an embodiment, a donor subject, a receiver subject, or both do not undergo Stage A preparation. In an embodiment, a donor subject, a receiver subject, or both do not undergo Stage B preparation. In an embodiment, a donor subject and a receiver subject, or both undergo Stage A and Stage B preparation.

Subsequent to administration of the mobilizer, and after a suitable time period has elapsed; a cell sample (e.g., donor cell sample or receiver cell sample) may be harvested from a subject. The time period between administration of the mobilizer to the subject and harvesting of the cell sample may be varied to meet one or more user and/or process goals. In an embodiment, the time period between administration of the mobilizer and harvesting of the cell sample may range from about 24 hours to about 10 days, alternatively from about 48 hours to about 7 days, or alternatively from about 3 days to about 5 days.

In an embodiment, the cell sample is harvested from a subject using any suitable methodology, for example, using an extracorporeal therapy such as apheresis. Apheresis is a method used to collect only a specific part of the subject's blood. It works on the basis of centrifugation or rapid spinning of the blood. A pathway is established for the subject's blood and allows for connection to the apheresis device. The instrument uses small pumps to move blood and fluids through the system. One pump draws blood out of one arm or side of the catheter and directs it to the centrifuge where the blood is separated into red cell, white cell, and plasma layers. A portion of the white cell layer, which includes stem cells, and a small amount of plasma and red cells are diverted to a collection bag. The rest of the blood is returned to the subject in the other arm or the second side of the catheter. In such an embodiment, the cell sample is harvested using intravenous needles located in a vein in each arm of a subject. Blood may be removed from a first vein, passed through an extracorporeal circuit that separates out the cell sample of interest and the remaining material may be returned to a second vein.

In an embodiment, the donor cell sample and/or receiver cell sample are harvested from the bone marrow directly. For example, the cell sample may be harvested from the iliac crest of a subject. In such embodiments, bone marrow aspiration to obtain the cell sample may involve a healthcare provider locating the posterior iliac crest of the subject subsequent to carrying out standard precautions such as skin sterilization and the administration of a local anesthetic. A suitable needle with the stylet in place may be slowly advanced through the skin and subcutaneous tissue pointing towards the anterior superior iliac spine. Upon reaching the posterior iliac crest, the area may be penetrated by the needle until an adequate depth is reached. Once the needle is in place, the stylet may be removed, a syringe attached, and the aspiration performed.

In an embodiment, a plurality of stem cell collections (e.g., bone marrow aspirations) is carried out in order to obtain some user and/or process desired number of cells in the cell sample. For example, the number of cells collected may range from $1 \times 10^6$-$1.0 \times 10^9$ cells/kg of the subject weight, alternatively from about $2 \times 10^6$-$1.0 \times 10^8$ cells/kg of the subject weight, or alternatively from about $5 \times 10^6$-$1.0 \times 10^8$ cells/kg of the subject weight. Cell samples harvested as disclosed herein may be utilized without further processing in the methodologies disclosed herein. Alternatively, cell samples harvested as disclosed herein may be further processed using any methodology compatible with the compositions and methodologies disclosed herein. Alternatively, cell samples harvested as disclosed herein may be stored for some time period before being utilized in the methodologies and therapies disclosed herein. Storage of the cell samples may involve, for example, cryogenic preservation of the cell sample in a biocompatible solution to stabilize the sample for the duration of storage. "Biocompatible solution" refers to solutions in which the cell sample (e.g., donor and/or receiver) are suspended for use in the cellular restoration methodologies disclosed herein or for any other subsequent uses. Such biocompatible solutions may include saline and may further comprise other ingredients such as preservatives, antimicrobials, and the like.

In an embodiment, cell samples harvested as disclosed herein are stored for greater than about 24 hours prior to being utilized in the methodologies disclosed herein. Alternatively, the cell samples harvested as disclosed herein are stored for a period of time ranging from about 1 hour to about 20 years prior to being utilized in the methodologies disclosed herein. Alternatively, storage of a cell sample harvested as disclosed herein may be for a time period ranging from about 10 days to about 15 years, alternatively from about 30 days to about 10 years, or alternatively from about 30 days to about 5 years.

As will be understood by the ordinarily skilled artisan, the donor cell sample and/or receiver cell sample, as harvested, comprise a heterogeneous cell population. An aspect of the methodologies disclosed herein comprises identifying and quantifying the types and amounts of cells present in the donor cell sample and/or receiver cell sample. Any methodology suitable for characterizing the number and types of cells present in the donor cell sample and/or receiver sample may be employed. In an embodiment, the donor cell sample and/or receiver cell sample are characterized by immunophenotyping. Herein, immunophenotyping refers to the analysis of heterogeneous populations of cells for the purpose of identifying the presence and proportions of the various populations in the sample. Antibodies are used to identify cells by detecting specific antigens (termed markers) expressed by these cells. In an embodiment, the donor cell sample and/or receiver sample are characterized by immunophenotyping using techniques such as flow cytometry. In alternative embodiments, characterizations of the various cell types present in a donor cell sample and/or receiver cell sample may be carried out using any suitable methodology such as reverse transcriptase polymerase chain reaction (RT-PCR) or immunocytochemistry.

In an embodiment, the populations of cells or cell types present in the donor cell sample and/or receiver cell sample are identified based on the presence or absence or one or more cell surface markers. An embodiment of a flow cytometry protocol for the identification of the different populations of cells (e.g., cell types) in a donor cell sample and/or receiver cell sample, 200, is presented in FIG. 1. Referring to FIG. 1, a cell sample (donor and/or receiver sample) 210 is subjected to flow cytometry. In an embodiment, the donor cell sample and/or receiver cell sample 210 may be, at a first stage, sorted into hematopoietic cells 220 and non-hematopoietic cells 230 based on the presence or absence of CD45. CD45, also known as leukocyte common antigen (LCA), T200, B220, Ly5, and protein tyrosine phosphatase receptor type C (PTPRC) is a transmembrane glycoprotein of the leukocyte-specific-receptor-like protein tyrosine phosphatase family. It is expressed on all nucleated hematopoietic cells and can cover up to 10% of the cell surface area. CD45 functions as a regulator of T-cell and B-cell antigen receptor signaling and is a regulator of cell growth and cell differentiation.

In an embodiment, CD45− cells, identified as non-hematopoietic stem cells 230, may be further characterized on the basis of the presence or absence of CD105. CD105, also known as endoglin, HHT1, ORW, and SH-1 is a type I membrane glycoprotein located on cell surfaces and is a component of the TGFβ receptor complex. CD105 may play a role in hematopoiesis and angiogenesis. In an embodiment, a cell population that is both CD45− and CD105+, 240, is characterized as having both mesenchymal stem cells and endothelial progenitor cells.

In an embodiment, a cell population that is identified to be both CD45− and CD105+, 240, may be further sorted into mesenchymal stem cells and endothelial progenitor cells. In an embodiment, the mesenchymal stem cells are identified as being CD45−, CD105+, CD29+ and CD44+, 250. CD29, also known as platelet GPIIa, integrin β1, and GP is an integrin unit associated with very late antigen receptors and functions in cell adhesion. CD44, also known as ECMRII, H-CAM, Pgp-1, HUTCH-1, Hermes antigen, phagocytic glycoprotein I, extracellular matrix receptor III, GP90 lymphocyte homing/adhesion receptor, and hyaluronate receptor functions in cell adhesion and migration. In an embodiment, endothelial progenitor cells are identified as being CD45−, CD105+, and CD31+, 260. CD31, also known as PECAM-1, endoCAM, platelet endothelial cell adhesion molecule, and PECA-1 is a protein that in humans is encoded by the PECAM1 gene found on chromosome 17. CD31 is thought to function in cell adhesion, activation, and migration.

The method of the present disclosure may further comprise identifying the differing hematopoietic cell types present in the CD45+ cells, 220. In an embodiment, a population of the cells is identified as being primitive hematopoietic stem cells, 270, on the basis of being CD45+, CD34+ and CD38−. In an embodiment, a population of the cells is identified as being hematopoietic progenitor cells on the basis of being CD45+, CD34+ and CD38+, 280. CD34 also known as gp105-120 and hematopoietic progenitor cell antigen (HPCA-1) is a member of the family of single-pass transmembrane sialomucin proteins that are expressed on early hematopoietic and vascular tissues. CD34 is thought to function in cell adhesion. CD38, also known as ADP-ribosyl cyclase, T10, and cyclic ADP-ribose hydrolase 1 is a multifunctional ectonucleotidase encoded by the CD38 gene which is located on chromosome 4. In an embodiment, at least a portion of the cell population are CD45+ and CD34−, 290, and are identified as differentiated hematopoietic cells. In such an embodiment, the differentiated hematopoietic cells, 290, may be further defined as being T-lymphocytes, 300, or Natural Killer cells, 310. T-lymphocytes can be characterized as being CD45+, CD34−, and CD3+. CD3, also known as T3, is a protein complex and plays a role in cell adhesion between T-cells and other cell types. Natural Killer cells can be characterized as being CD45+, CD34−, and CD56+. CD56 also known as Leu-19, NKH-1, and neural cell adhesion molecule (NCAM) is a hemophilic binding glycoprotein that may function in cell-cell adhesion, neurite outgrowth, synaptic plasticity, and learning and memory.

In an embodiment, the donor cell sample and/or receiver sample may be characterized using the methodologies disclosed herein. Such characterizations may result in the identification of cell populations in the donor cell sample and/or receiver cell sample that include without limitation, non-hematopoietic cells, mesenchymal stem cells, endothelial progenitor cells, hematopoietic cells, primitive hematopoietic stem cells, hematopoietic progenitor cells, differentiated hematopoietic cells, T-lymphocytes, natural killer cells, or combinations thereof. It is contemplated that the surface markers described herein represent one methodology for the identification of cell populations present within the donor cell sample and/or receiver cell sample. As will be understood by the ordinarily skilled artisan, numerous markers and combination of markers other than those disclosed herein may be utilized to identify and characterize the cell populations present within the donor cell sample and/or receiver cell sample. Further, the identification of the various cell populations present in the donor cell sample and/or receiver cell sample may be carried out to the extent described herein, may include determination of the presence or absence of additional surface markers, may utilize fewer markers than disclosed herein, or may be carried out to a lesser extent such that fewer populations of cells within the donor cell sample and/or receiver cell sample are identified. In an embodiment, a method comprises excluding the identification of the different populations of cells present in a donor cell sample and/or receiver cell sample.

In an embodiment, a donor cell sample and/or receiver cell sample is obtained from a subject having undergone a Stage B preparation. In such embodiments, the donor cell sample and/or receiver cell sample may be further characterized based on the number of senescent cells and non-senescent cells present in the cell sample. Herein, non-senescent cells refer to the cells that retain the ability to divide many times over without showing replicative senescence. Herein senescent cells refer to cells having a long-term loss of proliferative capacity despite continued viability and metabolic activity.

Senescent cells may be identified using a variety of metrics that include for example loss of proliferation, morphological changes, decreased telomere lengths, increased S-β-GAL activity, the production of senescence-associated heterochromatic foci (SAHF), increased production of senescence-associated secretory factors (SASF), increased production of reactive oxygen species (ROS), increased DNA damage, decreased chaperone-mediated autophagy, or combinations thereof. It is contemplated that changes in the various metrics described are assessed relative to comparable cell types established to be non-senescent cells. Alternatively, the characteristics of the cell sample may be compared to literature values established for the analyzed metric in a corresponding non-senescent cell.

Non-senescent cells may characterized by the length of their telomeres and of the level of telomerase activity present in the cell. By way of a non-limiting example, non-senescent cells present in the donor cell sample may be characterized by telomere lengths greater than or equal to about 4 kilobases, alternatively 4.5 kilobases, or alternatively 5 kilobases. It will be understood by the ordinarily skilled artisan that teleomere lengths indicative of non-senescent cells may vary depending on the cell type. Consequently, for a particular cell type, the telomere length characteristic of a non-senescent cell may be determined by routine experimentation.

In an embodiment, Stage B preparation of the subject from which the donor cell sample and/or receiver cell sample is harvested results in the preferential mobilization of non-senescent cells. The result of the preferential mobilization of non-senescent cells may be a donor cell sample and/or receiver cell sample comprising greater than 90% non-senescent cells, alternatively greater than 91% non-senescent cells, alternatively greater than 92% non-senescent cells, alternatively greater than 93% non-senescent cells, alternatively greater than 94% non-senescent cells, alternatively greater than 95% non-senescent cells, alternatively greater than 96% non-senescent cells, alternatively greater than 97% non-senescent cells, alternatively greater than 98% non-senescent cells, or alternatively greater than 99% non-senescent cells. The percentage of non-senescent cells is based on the total number of cells present in the sample. In an embodiment, the donor cell sample and/or receiver cell sample comprise from about 90% non-senescent cells to about 99% non-senescent cells based on the total number of cells present in the sample.

In some embodiments, the non-senescent cells present in the donor cell sample and/or receiver cell sample may be identified using any suitable methodology. In such embodiments, the non-senescent cells may be separated from the senescent cells using any suitable process compatible with the present disclosure to result in a donor cell sample and/or receiver cell sample that comprises, consists essentially of, or consists of non-senescent cells. It is contemplated that such methodologies may be extended to further define a population of non-senescent cells having the presence or absence of particular cell surface markers and result in a donor cell sample and/or receiver cell sample comprising, consisting essentially of, or consisting of non-senescent cells of a particular type (e.g., non-senescent mesenchymal stem cells, non-senescent natural killer cells).

In an embodiment, the donor cell sample and/or receiver cell sample may be analyzed for the extent of expression of one or more genes and/or proteins associated with cellular senescence. Such analyses may be carried out using a restoration biomarker protein panel (RBPP) and/or restoration biomarker gene expression panel (RBGEP) of the types disclosed herein.

In an embodiment, the RBPP comprises a plurality of antibody probes for factors linked to cellular aging and senescence. For example, the RBPP may comprise greater than 5 antibody probes, alternatively greater than 10 antibody probes, or alternatively greater than 20 antibody probes. In an embodiment the RBPP comprises from 10 to 15 antibody probes. An example of a RBPP suitable for use in this disclosure is a protein array panel designated RBPP-X1 comprising antibody probes to the proteins listed in Table 1:

TABLE 1

| Name | Also Known As | Designated |
|---|---|---|
| granulocyte-colony stimulating factor | colony-stimulating factor 3 | G-CSF |
| chemokine ligand 26 | eotaxin-3, macrophage inflammatory protein 4-alpha, thymic stroma chemokine, and IMAC | CCL26 |
| hepatocyte growth factor | hepatocyte scatter factor (HSF), | HGF |
| insulin-like growth factor binding protein 1 | placental protein 12 (PP12) | IGFBP-1 |
| insulin-like growth factor binding protein 4 | | IGFBP-4 |
| insulin-like growth factor binding protein 6 | | IGFBP-6 |
| insulin-like growth factor beta | catabolin | IL-β |
| macrophage inflammatory protein 3 (MIP3A) | chemokine ligand 20, liver activation regulated chemokine (LARC) | MCP-3α |
| stem cell factor | KIT-ligand, KL, steel factor | SCF |
| thymus and activation regulated chemokine | chemokine ligand 17 (CCL17), | TARC |
| transforming growth factor beta 1 | | TGF-β1 |
| tumor necrosis factor receptor superfamily member 1A | | sTNFR1 |
| vascular endothelial growth factor | | VEGF |

In an embodiment, the RBGEP may comprise greater than 5 gene probes, alternatively greater than 10 gene probes, or alternatively, greater than 20 gene probes. In an embodiment, the RBGEP comprises from 10 to 15 gene probes. In some embodiments, the RBGEP comprises gene probes for factors linked to the regulation of cell cycle or the p53 pathway such as IFBP3, CSC25C, ABL1, CDKN2B, ALDH1A3, SIRT1, ING1, CITED2, and CDKN1C. The RBGEP may further comprise gene probes for factors associated with regulation of inflammatory processes such as CDKN1A, IRF3, EGR1, IFNG, CDKN1B, NFKB1, SERPING2, IGFBP7, and IRF7. The RBGEP may further comprise gene probes for factors associated with regulation of DNA damage related-processes such as PCNA, TERT, and TP53BP1. The RBGEP may further comprise gene probes for factors associated with oxidative stress such as PRKCD, SOD1, and NOX4. The RBGEP may further comprise gene probes for factors associated with cellular senescence such as CDKN2A, CDK6, TWIST, ATM, CCND1, ETS2, RBL2, BMI1, and ETS1. The RBGEP may further comprise gene probes for factors associated with the MAPK pathway such as HRAS and MAP2K3. The RBGEP may further comprise gene probes for factors associated with cytoskeletal function such as VIM, PIK3CA, and THBS1. The RBGEP may further comprise gene probes for factors associated with the p16 effector pathway such as TBX3 and TBX2. The RBGEP may further comprise gene probes for factors associated with insulin signaling such as IGFBP5. The RBGEP may further comprise gene probes for factors associated with cell adhesion such as CDL3A1, CD44, TGFB1A, CDL1A1 and TGFB1. The RBGEP may further comprise gene probes for factors associated with the p53 effector pathway such as E2F1 and MYC. An example of a RBGEP suitable for use in this disclosure, designated RBGEP-X1, is a gene panel comprising cDNA to the proteins listed in Table 2:

TABLE 2

| Gene | Protein Encoded |
| --- | --- |
| IGFBP3 | insulin-like growth factor binding protein 3 |
| HRAS | Transforming protein p21 |
| PRKCD | protein kinase C delta |
| AKT1 | alpha serine/threonine protein kinase |
| CHEK2 | checkpoint kinase 2 |
| MAPK14 | mitogen-activated protein kinase 14 |
| IGF1 | insulin-like growth factor |
| TWIST1 | Twist-related protein 1 |
| CDC25C | M-phase inducer phosphatase 3 |
| CCNA2 | cyclin-A2 |
| CDK5 | cell-division protein kinase 6 |
| CCNE1 | G1/S-specific cyclin E1 |
| CHEK1 | checkpoint kinase 1 |

In an embodiment, at least a portion of the donor cell sample and/or receiver cell sample are subjected to protein array analyses utilizing the RBPP-X1 array, gene expression analysis using the RBGEP-X1 array, or both. In alternative embodiments, at least a portion of the donor cell sample and/or receiver cell sample are subjected to protein array analyses, gene expression analyses or both utilizing any suitable protein and/or gene array.

In an embodiment, the donor cell sample, receiver cell sample, or both are subjected to at least one analytical technique to characterize the quality of the cell sample. Herein, the "quality" of the cell sample refers to factors used to characterize the cellular health of the sample and includes parameters such as the number and types of cells present in the sample; the ratio of senescent to non-senescent cells in the sample; the extent of expression of a group of genetic and/or protein biomarkers; the average telomere length of the cells in the sample; and the status of the innate immune function of the cells in the sample. Telomere length may be determined using any suitable methodology, for example, terminal restriction fragment (TRF) analysis. Innate immune function may be evaluated using any suitable methodology such as the $^{51}$Cr cytotoxicity release natural killer cell assay. The donor cell sample quality may be an assessment of the ability of the cells in the sample to improve and/or restore one or more cellular functions of the cells in the receiver cell sample. The receiver cell sample quality may be an assessment of the ability of the cells in the sample to exhibit improvement and/or the restoration of one or more cellular functions when subjected to the compositions and methodologies disclosed herein.

The donor cell sample quality may be assigned a numerical value that ranges from 1 to 10 wherein a sample displaying positive characteristics for use in the improvement and/or restoration of cellular function of a receiver cell sample has a value of 10, and a sample exhibiting the fewest characteristics associated with the ability to improve/restore cellular function of a receiver cell sample has a value of 1. For example, each of the following factors may weigh positively in characterization of the quality of a donor cell sample; relatively long telomere length; high level of expression of cell viability-promoting genes and/or proteins; the presence of greater than about 90% non-senescent cells; and high levels of innate immune function. Donor cell samples displaying these characteristics may be given a sample quality value of 10.

The receiver cell sample quality may be assigned a numerical value that ranges from 1 to 10 wherein a sample having restorable or improvable cellular function has a value of 10, and a sample whose cellular function cannot be significantly improved and/or restored has a value of 1. For example, each of the following factors may weigh positively in characterization of the quality of a receiver cell sample; relatively long telomere length; moderate level of expression of senescence-promoting genes and/or proteins; and the presence of greater than about 90% non-senescent cells. Receiver cell samples displaying these characteristics may be given a sample quality value of 10.

Utilizing the quality metrics disclosed herein (e.g., telomere length, percentage of non-senescent cells), an aspect of the present disclosure comprises evaluating the quality of the donor cell sample and receiver cell sample and identifying samples suitable for use in the disclosed methodologies. For example, a receiver cell sample having a quality value of less than 3 may be deemed unsuitable for use in the presently disclosed methodologies. Similarly, a donor cell sample having a quality value of less than 3 may be deemed unsuitable for use in the present methodologies. In some embodiments, the a donor cell sample having a quality value of equal to or greater than 7 may be used in the methodologies disclosed herein with a receiver cell sample having a quality value of equal to or greater than 7. It is to be understood that the quality values may be assigned based on any number of metrics used to assess the quality of a donor cell sample and/or receiver cell sample. Consequently, based on the parameters used to make the assignment of a quality value, the characteristics associated with a particular quality value may differ.

In some embodiments, the donor cell sample and/or receiver cell sample having been subjected to one or more of the qualitative and quantitative characterizations described herein are further processed to provide some user and/or process desired sample containing a predetermined type and number of cells. The present disclosure contemplates the utilization of such characterized samples. For example, the characterized samples may be a component of a pharmaceutical formulation that is administered to a subject to ameliorate one or more medical conditions.

Alternatively, the donor cell sample and receiver cell sample may be utilized in the restoration methodologies disclosed herein.

In an embodiment, a method of cellular restoration comprises contacting the soluble factors and/or particles present in the media of a cultured donor cell sample with the receiver cell sample. For example, the donor cell sample may be cultured in appropriate media for a time period ranging from about 24 hours to about 6 weeks, alternatively, from about 1 week to about 5 weeks or alternatively, from about 2 weeks to about 4 weeks. Herein, the culture media, also known as the growth media, refers to a liquid or gel containing the appropriate nutrients to support the growth of cells. Suitable culture media may be chosen by the ordinarily skilled artisan with the benefits of the present disclosure.

The culture media may then be removed from the donor cell sample using any suitable methodology (e.g., filtration, centrifugation) and the cell-free media then contacted with the receiver cell sample.

Figure 2:
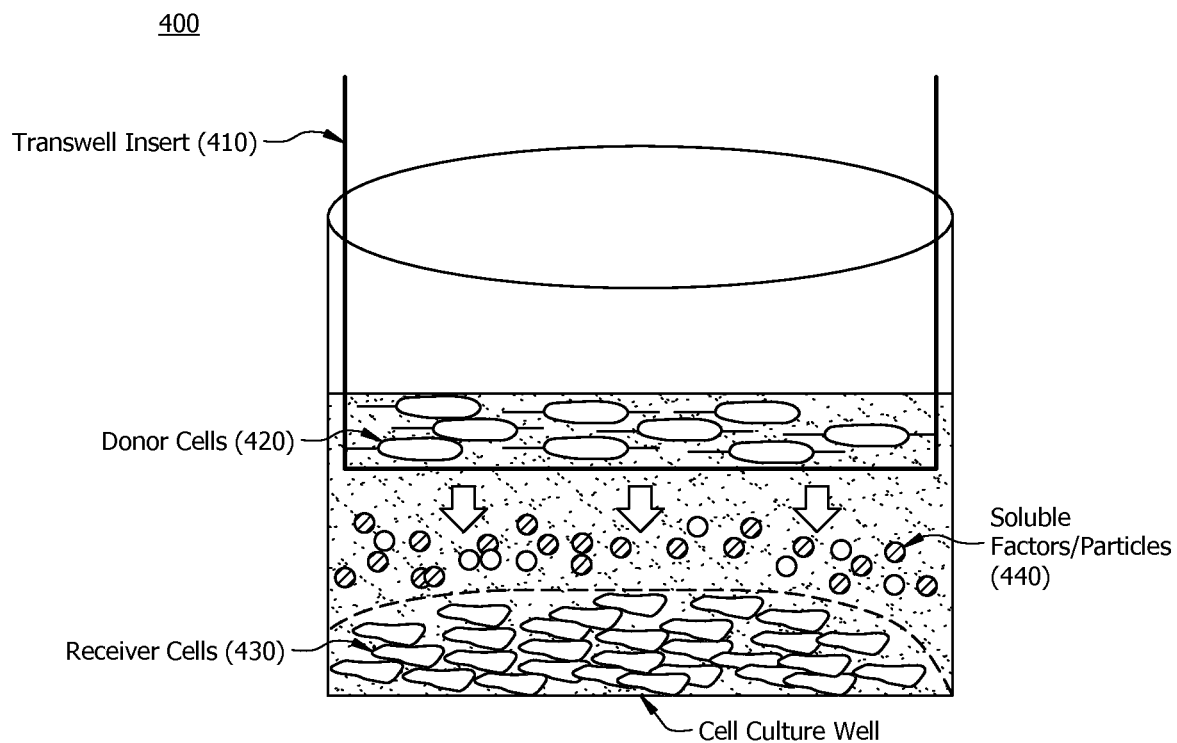
FIG. 2 is a depiction of an embodiment of a transwell co-culture experimental apparatus.

In an alternative embodiment, the method of cellular restoration comprises establishing a transwell culture of both the donor cell sample and receiver cell sample. Referring to FIG. 2, the transwell culture 400 may comprise an insert 410 having at least one permeable surface that allows the donor cells to uptake and secrete molecules on the basal and/or apical surfaces of the transwell. The transwell insert 410 may be comprised of any material compatible with the compositions and methodologies disclosed herein such as, for example, polyethylene terephthalate or polycarbonate. In an embodiment, the transwell insert 410 comprises a permeable membrane with a pore size ranging from 0.4 μm to 3.0 μm, alternatively from 0.4 μm to 2.0 μm, or alternatively from 0.4 μm to 1.0 μm. The transwell insert may have a pore size that allows for the passage of soluble factors and/or particles secreted or released from the donor cell sample to the lower compartment of the transwell where these materials contact the receiver cell sample. At least a portion of the donor cell sample 420 may be applied to the transwell insert 410 while the receiver cell sample 430 is positioned within the lower compartment of the transwell culture with an appropriate amount of culture media. The donor cell sample and receiver cell sample may be cultured in the transwell for a time period of from 24 hours to 6 weeks, alternatively, from 1 week to 5 weeks, or alternatively, from 2 weeks to 4 weeks. Soluble factors and/or particles of the appropriate size 440 are allowed to pass through the permeable membrane and contact the receiver cell sample 430 in the lower chamber of the transwell.

In an embodiment, the donor cell sample and receiver cell sample are recovered separately from the transwell culture. The donor cell sample, as recovered from the transwell culture, is hereinafter termed the altered donor cell sample (ADCS). The receiver cell sample as recovered from the transwell culture is termed the restored composition (RC). In an embodiment, the ADCS and/or RC may be further characterized using any of the methodologies disclosed herein. In some embodiments, at least a portion of the ADCS and/or RC are further processed, for example, the samples may be prepared for cryopreservation. In yet another embodiment, at least a portion of the RC is utilized to treat a subject.

Herein the RC refers to the cellular material subsequent to culturing with the soluble factors of the donor cell sample for the time periods disclosed herein. The RC is characterized by improvement in one or more of the following metrics when compared to the receiver cell sample; innate immune function, morphology, colony-forming ability, reduced expression of senescence-promoting factors; increased expression of cell-viability promoting factors, and the like. In an embodiment, the RC is characterized by the presence of cells having gene expression and protein expression patterns for cellular senescence associated agents (e.g., CDKN2A, CDK6, TWIST, ATM, CCND1, ETS2, RBL2, BMI1, and ETS1) that are quantitatively more similar to those of the donor cell sample than the receiver cell sample.

In one embodiment, a methodology disclosed herein comprises the preparation of a RC. The RC is derived from the receiver cell sample that is subjected to the methodologies disclosed herein, specifically by the restoration of at least a portion of the receiver cell sample. Herein, "restoration" refers to modification of a cell (e.g., stem cell) such that expression of one or more senescence-promoting agents is reduced and/or expression of one or more cell viability/cell function-promoting agents is increased. Without wishing to be limited by theory, the methodologies and compositions disclosed herein may result in the epigenetic modification of one or more cell types that results in at least one characteristic associated with improved cellular function when compared to an otherwise similar cell type not subjected to the compositions and methods disclosed herein. Herein, "epigenetic" refers to the heritable changes in gene activity and expression that occurs without alternation in DNA sequence. Nonlimiting examples of epigenetic modifications include posttranslational modifications such as DNA methylation, chromatin remodeling, and histone modification.

The RC comprises cells that may exhibit alterations in parameters of cellular and/or organismal physiology that result in a perceived and/or quantifiable improvement in the functional state of receiver cells and/or cell types, wherein perceived improvement is defined as semblance to the functional state of the donor cells and/or cell types. It is to be understood that the restored composition comprises cells and is derived from a corresponding receiver cell sample.

In an embodiment, a RC is characterized by the maintenance of the viability state of the cells and/or cell types in the composition as quantified, for example, by a cell vitality assay.

In an alternate embodiment, a RC is characterized by an increase in the viability state of the cells and/or cell types as quantified, for example, by a cell viability assay.

In an embodiment, a RC is characterized by a lack of change in the percentage of hematopoietic stem cells, hematopoietic progenitor cells, mesenchymal stem cells and endothelial progenitor cells, herein termed the "stem cell pool", compared to the receiver cell sample.

In an alternate embodiment, a RC is characterized by an increase in the stem cell pool in comparison to the receiver cell sample.

In an embodiment, a RC is characterized by cells that exhibit an improvement in cellular immune function in comparison to the corresponding receiver cell sample as quantified, for example, by natural killer cell cytotoxicity assay.

In an embodiment, a RC is characterized by cells that exhibit an improvement in cellular hematopoietic function as quantified, for example, by hematopoietic stem cell clonogenic assay in comparison to the corresponding receiver cell sample.

In an alternate embodiment, a RC is characterized by cells that exhibit an improvement in systematic hematopoietic and immune function of the subject when compared to the corresponding receiver cell sample as quantified, for example, by increased lymphopoiesis, increased ratio of CD4 to CD8 positive T cells, and/or improved immune surveillance. Improved immune surveillance can be determined by decreased incidences of microbial infection and tumor formation in the subject. Improved immune surveillance can also be measured by decreased rate of cancer incidence in the subject. Decreased rates of cancer incidence shall thereby confer to the subject an increased likelihood of prolonged organismal survival.

In an embodiment, a RC is characterized by cells that exhibit a minimization of replicative stress as determined, for example, by telomere length and/or telomerase activity when compared to the corresponding receiver cell sample.

In an embodiment, a RC is characterized by cells that exhibit a decreased expression of senescence-related genes when compared to the corresponding receiver cell sample, wherein senescence-related genes are defined, for example, as the RBGEP, by quantitative polymerase chain reaction.

In an embodiment, a RC is characterized by cells that exhibit a decreased expression of senescence-associated secretory factors when compared to the corresponding receiver cell sample, wherein senescence-associated secretory factors are exemplified in Table 1.

In an embodiment, a RC is characterized by cells that exhibit alterations in the epigenetic signature of the cells when compared to the corresponding receiver cell sample, wherein epigenetic signature is determined, for example, by chromatin immunoprecipitation sequencing (ChIP-Seq).

In an embodiment, a RC is characterized by cells that exhibit an increase in the rate of proteostasis when compared to the corresponding receiver cell sample which may be quantified, for example, by a Cyto-ID® Autogphagy Detection Kit.

In an embodiment, a RC is characterized by cells that exhibit a decrease in cellular oxidative stress when compared to the corresponding receiver cell sample, as quantified for example by the MitoSOX™ Red mitochondrial superoxide indicator kit.

In an embodiment, a RC is characterized by cells that exhibit a decrease in cellular senescence when compared to the corresponding receiver cell sample, as quantified, for example, by the Fluorometric Quantitative Cellular Senescence β-Gal Assay Kit.

In an embodiment, a RC is characterized by cells that exhibit the maintenance of mesenchymal stem cell function when compared to the corresponding receiver cell sample, wherein mesenchymal stem cell function is quantified, for example, by the colony forming unit-fibroblast (CFU-F) assay and/or ability to undergo lineage-specific differentiation into adipogenic, osteogenic and chondrogenic lineages.

In an alternate embodiment, a RC is characterized by cells that exhibit an increased mesenchymal stem cell function when compared to the corresponding receiver cell sample.

In an embodiment, a RC is characterized by cells that exhibit maintenance of endothelial progenitor function when compared to the corresponding receiver cell sample wherein endothelial progenitor function is quantified, for example, by tube formation assay.

In an alternate embodiment, a RC is characterized by cells that exhibit an increased endothelial progenitor function when compared to the corresponding receiver cell sample.

Herein, cellular restoration occurs following contact of the receiver cell sample with soluble factors and/or particles present in the donor cell sample (e.g., materials that pass through the permeable transwell insert). Consequently, the method of restoration comprises contact of the cell-free soluble factors and/or particles present in the media of a donor cell sample with a receiver cell sample. In some embodiments, the donor cell sample is cultured in a suitable media and the media may then be separated from the donor cells to form a cell-free media which is utilized in the restoration of a receiver cell sample. Without wishing to be limited by theory, the soluble factors and/or particles present in the donor cell sample media that pass through the permeable transwell insert may include paracrine factors, microvesicles, exosomes, cellular fragments, and the like. Herein paracrine factors refer to signaling molecules which are secreted into the immediate extracellular environment and diffuse over a short distance to a target cell. Microvesicles generally refer to small (e.g., 50 nm to 100 nm) fragments of plasma membrane thought to be shed by a variety of cell types. Exosomes generally refer to secreted extracellular vesicles that may contain biomolecules such as proteins, lipids, and RNA and function in cellular signaling. In an embodiment, the soluble factors and/or particles of the donor cell sample that contact the receiver cell sample comprise extracellular vesicles. Exosomes and microvesicles belong to a broader group of extracellular vesicles (EVs) that represent an important mode of intercellular communication by serving as vehicles for transfer between cells of membrane and cytosolic proteins, lipids, and RNA.

In an embodiment, the quality of the restoring composition can be adjusted by the presence of one or more materials that regulate the release of EVs. For example, the release of one or more EVs may be inhibited by the addition of small molecule inhibitors such as mannumycin A. Alternatively, the release of EVs may be promoted, for example, by activation of purinergic receptors with ATP, activation by lipopolysaccharides, plasma membrane depolarization, or increasing intracellular $Ca^{2+}$ concentrations.

It is a contemplated aspect of the present disclosure that cell-free media generated by culturing of the donor cell sample in a suitable media followed by removal of the cells and herein designated the restoring composition, may be further processed to separate individual constituents or groups of constituents based on like characteristics using any suitable methodology (e.g., ethanol precipitation, centrifugation gradients). In an embodiment, the individual constituents of the restoring composition may be analyzed for their ability to affect restoration of a receiver cell sample of the type disclosed herein. The present disclosure further contemplates utilization of one or more isolated constituents, or isolated groups of constituents, in the methodologies for cellular restoration. In an embodiment, cellular restoration of a receiver cell sample of the type disclosed herein is carried out utilizing an EV (e.g., exosome/microvesicle) isolated from a culture media of a donor cell sample. In another embodiment, cellular restoration of a receiver cell sample of the type disclosed herein is carried out utilizing cellular fragments isolated from a culture media of a donor cell sample.

In an embodiment, the RC may be formulated for administration to a subject in need thereof. In an embodiment, the subject is the receiver subject. For example, the RC may be a component of a formulation that is administered to the receiver subject to improve the receiver subject's general health. Such improvements may be identified by quantitative evaluation of one or more physiological or psychological parameters of the subject. In the alternative, such improvements may be identified by the qualitative evaluations of one or more physiological or psychological parameters of the subject. In an embodiment, the receiver subject is prophylactically administered the RC.

The RC may be administered to a subject (e.g., receiver subject) via any suitable methodology. In some embodiments, the methodologies disclosed herein comprise systemic administration of the RC to the subject. For example, the RC may be administered systemically in dosage unit formulations containing conventional nontoxic pharmaceutically acceptable carriers, adjuvants, and vehicles as desired. In a specific embodiment, administration of the RC may be by intravenous injection, endobronchial adminstration, intraaterial injection, intramuscular injection, intracardiac injection, subcutaneous injection, intraperitoneal injection, intraperitoneal infusion, transdermal diffusion, transmucosal diffusion, intracranial, intrathecal, or combinations thereof. A means of administering the RC may include, but is not limited to, infusion. Systemically may also include, for example, by a pump, by an intravenous line, or by bolus injection. Bolus injection can include subcutaneous, intramuscular, or intraperitoneal routes.

The phrases "systemic administration" or "administered systemically," as used herein, mean the administration of a compound(s) of the disclosure, composition, drug, or other material such that it enters the subject's system and, thus, is subject to metabolism and other like processes, for example, subcutaneous administration.

In other embodiments, the RC is locally administered by means such as, but not limited to, injection, implantation, grafting, or epicutaneous. For example, the RC may be administered proximal to a wound site on the subject and functions to ameliorate the symptoms associated with the wound or increase the rate of wound-healing. In yet other embodiments, the RC may be administered at or proximal to the site utilized to harvest the receiver cell sample from the subject. Administration of the RC may be conducted in any manner compatible with the compositions disclosed herein and to meet one or more user and/or process goals.

In an alternative embodiment, the subject (e.g., receiver subject) is administered the RC as a component of a therapeutic procedure designed to ameliorate the effects of a medical condition. In such embodiments, the RC, present in a therapeutically effective amount, may function as an active agent in a pharmaceutical composition. Such pharmaceutical compositions comprising the RC are hereinafter termed cellular material-based pharmaceutical compositions or CMBPC. Additional active agents may be present in the CMBPC as considered beneficial for the treatment of the medical condition. Examples of additional active agents include but are not limited to: (a) antimicrobials, (b) steroids (e.g., hydrocortisone, triamcinolone); (c) pain medications (e.g., aspirin, an NSAID, and a local anesthetic); (d) anti-inflammatory agents; (e) growth factors; (f) cytokines; (g) hormones; and (h) combinations thereof. Such additional active agents may also be present in a therapeutically effective amount.

Examples of additional active agents for inclusion in the CMBPC pharmaceutical or drug include, but are not limited to, anesthetics, hypnotics, sedatives and sleep inducers, antipsychotics, antidepressants, antiallergics, antianginals, antiarthritics, antiasthmatics, antidiabetics, antidiarrheal drugs, anticonvulsants, antigout drugs, antihistamines, antipruritics, emetics, antiemetics, antispasmodics, appetite suppressants, neuroactive substances, neurotransmitter agonists, antagonists, receptor blockers and reuptake modulators, beta-adrenergic blockers, calcium channel blockers, disulfuram and disulfuram-like drugs, muscle relaxants, analgesics, antipyretics, stimulants, anticholinesterase agents, parasympathomimetic agents, hormones, anticoagulants, antithrombotics, thrombolytics, immunoglobulins, immunosuppressants, hormone agonists/antagonists, vitamins, antimicrobial agents, antineoplastics, antacids, digestants, laxatives, cathartics, antiseptics, diuretics, disinfectants, fungicides, ectoparasiticides, antiparasitics, heavy metals, heavy metal antagonists, chelating agents, gases and vapors, alkaloids, salts, ions, autacoids, digitalis, cardiac glycosides, antiarrhythmics, antihypertensives, vasodilators, vasoconstrictors, antimuscarinics, ganglionic stimulating agents, ganglionic blocking agents, neuromuscular blocking agents, adrenergic nerve inhibitors, anti-oxidants, vitamins, cosmetics, anti-inflammatories, wound care products, anti-thrombogenic agents, antitumoral agents, antiangiogenic agents, anesthetics, antigenic agents, wound healing agents, plant extracts, growth factors, emollients, humectants, rejection/anti-rejection drugs, spermicides, conditioners, antibacterial agents, antifungal agents, antiviral agents, antibiotics, tranquilizers, cholesterol-reducing drugs, antitussives, histamine-blocking drugs, and monoamine oxidase inhibitor.

Specific compounds suitable for use in the CMBPC include silver sulfadiazine, Nystatin, Nystatin/triamcinolone, Bacitracin, nitrofurazone, nitrofurantoin, a polymyxin (e.g., Colistin, Surfactin, Polymyxin E, and Polymyxin B), doxycycline, antimicrobial peptides (e.g., natural and synthetic origin), NEOSPORIN® (i.e., Bacitracin, Polymyxin B, and Neomycin), POLYSPORIN® (i.e., Bacitracin and Polymyxin B). Additional antimicrobials include topical antimicrobials (i.e., antiseptics), examples of which include silver salts, iodine, benzalkonium chloride, alcohol, hydrogen peroxide, chlorhexidine, acetaminophen; Alfentanil Hydrochloride; Aminobenzoate Potassium; Aminobenzoate Sodium; Anidoxime; Anileridine; Anileridine Hydrochloride; Anilopam Hydrochloride; Anirolac; Antipyrine; Aspirin; Benoxaprofen; Benzydamine Hydrochloride; Bicifadine Hydrochloride; Brifentanil Hydrochloride; Bromadoline Maleate; Bromfenac Sodium; Buprenorphine Hydrochloride; Butacetin; Butixirate; Butorphanol; Butorphanol Tartrate; Carbamazepine; Carbaspirin Calcium; Carbiphene Hydrochloride; Carfentanil Citrate; Ciprefadol Succinate; Ciramadol; Ciramadol Hydrochloride; Clonixeril; Clonixin; Codeine; Codeine Phosphate; Codeine Sulfate; Conorphone Hydrochloride; Cyclazocine; Dexoxadrol Hydrochloride; Dexpemedolac; Dezocine; Diflunisal; Dihydrocodeine Bitartrate; Dimefadane; Dipyrone; Doxpicomine Hydrochloride; Drinidene; Enadoline Hydrochloride; Epirizole; Ergotamine Tartrate; Ethoxazene Hydrochloride; Etofenamate; Eugenol; Fenoprofen; Fenoprofen Calcium; Fentanyl Citrate; Floctafenine; Flufenisal; Flunixin; Flunixin Meglumine; Flupirtine Maleate; Fluproquazone; Fluradoline Hydrochloride; Flurbiprofen; Hydromorphone Hydrochloride; Ibufenac; Indoprofen; Ketazocine; Ketorfanol; Ketorolac Tromethamine; Letimide Hydrochloride; Levomethadyl Acetate; Levomethadyl Acetate Hydrochloride; Levonantradol Hydrochloride; Levorphanol Tartrate; Lofemizole Hydrochloride; Lofentanil Oxalate; Lorcinadol; Lomoxicam; Magnesium Salicylate; Mefenamic Acid; Menabitan Hydrochloride; Meperidine Hydrochloride; Meptazinol Hydrochloride; Methadone Hydrochloride; Methadyl Acetate; Methopholine; Methotrimeprazine; Metkephamid Acetate; Mimbane Hydrochloride; Mirfentanil Hydrochloride; Molinazone; Morphine Sulfate; Moxazocine; Nabitan Hydrochloride; Nalbuphine Hydrochloride; Nalmexone Hydrochloride; Namoxyrate; Nantradol Hydrochloride; Naproxen; Naproxen Sodium; Naproxol; Nefopam Hydrochloride; Nexeridine Hydrochloride; Noracymethadol Hydrochloride; Ocfentanil Hydrochloride; Octazamide; Olvanil; Oxetorone Fumarate; Oxycodone; Oxycodone Hydrochloride; Oxycodone Terephthalate; Oxymorphone Hydrochloride; Pemedolac; Pentamorphone; Pentazocine; Pentazocine Hydrochloride; Pentazocine Lactate; Phenazopyridine Hydrochloride; Phenyramidol Hydrochloride; Picenadol Hydrochloride; Pinadoline; Pirfenidone; Piroxicam Olamine; Pravadoline Maleate; Prodilidine Hydrochloride; Profadol Hydrochloride; Propirarn Fumarate; Propoxyphene Hydrochloride; Propoxyphene Napsylate; Proxazole; Proxazole Citrate; Proxorphan Tartrate; Pyrroliphene Hydrochloride; Remifentanil Hydrochloride; Salcolex; Salethamide Maleate; Salicylamide; Salicylate Meglumine; Salsalate; Sodium Salicylate; Spiradoline Mesylate; Sufentanil; Sufentanil Citrate; Talmetacin; Talniflumate; Talosalate; Tazadolene Succinate; Tebufelone; Tetrydamine; Tifurac Sodium; Tilidine Hydrochloride; Tiopinac; Tonazocine Mesylate; Tramadol Hydrochloride; Trefentanil Hydrochloride; Trolamine; Veradoline Hydrochloride; Verilopam Hydrochloride; Volazocine; Xorphanol Mesylate; Xylazine Hydrochloride; Zenazocine Mesylate; Zomepirac Sodium; Zucapsaicin., Aflyzosin Hydrochloride; Alipamide; Althiazide; Amiquinsin Hydrochloride; Amlodipine Besylate; Amlodipine Maleate; Anaritide Acetate; Atiprosin Maleate; Belfosdil; Bemitradine; Bendacalol Mesylate; Bendroflumethiazide; Benzthiazide; Betaxolol Hydrochloride; Bethanidine Sulfate; Bevantolol Hydrochloride; Biclodil Hydrochloride; Bisoprolol; Bisoprolol Fumarate; Bucindolol Hydrochloride; Bupicomide; Buthiazide: Candoxatril; Candoxatrilat; Captopril; Carvedilol; Ceronapril; Chlorothiazide Sodium; Cicletanine; Cilazapril; Clonidine; Clonidine Hydrochloride; Clopamide; Cyclopenthiazide; Cyclothiazide; Darodipine; Debrisoquin Sulfate; Delapril Hydrochloride; Diapamide; Diazoxide; Dilevalol Hydrochloride; Diltiazem Malate; Ditekiren; Doxazosin Mesylate; Eeadotril; Enalapril Maleate; Enalaprilat; Enalkiren; Endralazine Mesylate; Epithiazide; Eprosartan; Eprosartan Mesylate; Fenoldopam Mesylate; Flavodilol Maleate; Flordipine; Flosequinan; Fosinopril Sodium; Fosinoprilat; Guanabenz; Guanabenz Acetate; Guanacline Sulfate; Guanadrel Sulfate; Guancydine; Guanethidine Monosulfate; Guanethidine Sulfate; Guanfacine Hydrochloride; Guanisoquin Sulfate; Guanoclor Sulfate; Guanoctine Hydrochloride; Guanoxabenz; Guanoxan Sulfate; Guanoxyfen Sulfate; Hydralazine Hydrochloride; Hydralazine Polistirex; Hydroflumethiazide; Indacrinone; Indapamide; Indolaprif Hydrochloride; Indoramin; Indoramin Hydrochloride; Indorenate Hydrochloride; Lacidipine; Leniquinsin; Levcromakalim; Lisinopril; Lofexidine Hydrochloride; Losartan Potassium; Losulazine Hydrochloride; Mebutamate; Mecamylamine Hydrochloride; Medroxalol; Medroxalol Hydrochloride; Methalthiazide; Methyclothiazide; Methyldopa; Methyldopate Hydrochloride; Metipranolol; Metolazone; Metoprolol Fumarate; Metoprolol Succinate; Metyrosine; Minoxidil; Monatepil Maleate; Muzolimine; Nebivolol; Nitrendipine; Ofornine; Pargyline Hydrochloride; Pazoxide; Pelanserin Hydrochloride; Perindopril Erbumine; Phenoxybenzamine Hydrochloride; Pinacidil; Pivopril; Polythiazide; Prazosin Hydrochloride; Primidolol; Prizidilol Hydrochloride; Quinapril Hydrochloride; Quinaprilat; Quinazosin Hydrochloride; Quinelorane Hydrochloride; Quinpirole Hydrochloride; Quinuclium Bromide; Ramipril; Rauwolfia Serpentina; Reserpine; Saprisartan Potassium; Saralasin Acetate; Sodium Nitroprusside; Sulfinalol Hydrochloride; Tasosartan; Teludipine Hydrochloride; Temocapril Hydrochloride; Terazosin Hydrochloride; Terlakiren; Tiamenidine; Tiamenidine Hydrochloride; Tierynafen; Tinabinol; Tiodazosin; Tipentosin Hydrochloride; Trichlormethiazide; Trimazosin Hydrochloride; Trimethaphan Camsylate; Trimoxamine Hydrochloride; Tripamide; Xipamide; Zankiren Hydrochloride; Zofenoprilat Arginine., Alclofenac; Alclometasone Dipropionate; Algestone Acetonide; Alpha Amylase; Ameinafal; Ameinafide; Amfenac Sodium; Amiprilose Hydrochloride; Anakinra; Anirolac; Anitrazafen; Apazone; Balsalazide Disodium; Bendazac; Benoxaprofen; Benzydamine Hydrochloride; Bromelains; Broperamole; Budesonide; Carprofen; Cicloprofen; Cintazone; Cliprofen; Clobetasol Propionate; Clobetasone Butyrate; Clopirac; Cloticasone Propionate; Cormethasone Acetate; Cortodoxone; Deflazacort; Desonide; Desoximetasone; Dexamethasone Dipropionate; Diclofenac Potassium; Diclofenac Sodium; Diflorasone Diacetate; Diflumidone Sodium; Diflunisal; Difluprednate; Diftalone; Dimethyl Sulfoxide; Drocinonide; Endrysone; Enlimomab; Enolicam Sodium; Epirizole; Etodolac; Etofenamate; Felbinac; Fenamole; Fenbufen; Fenclofenac; Fenclorac; Fendosal; Fenpipalone; Fentiazac; Flazalone; Fluazacort; Flufenamic Acid; Flumizole; Flunisolide Acetate; Flunixin; Flunixin Meglumine; Fluocortin Butyl; Fluorometholone Acetate; Fluquazone; Flurbiprofen; Fluretofen; Fluticasone Propionate; Furaprofen; Furobufen; Halcinonide; Halobetasol Propionate; Halopredone Acetate; Ibufenac; Ibuprofen; Ibuprofen Aluminum; Ibuprofen Piconol; Ilonidap; Indomethacin; Indomethacin Sodium; Indoprofen; Indoxole; Intrazole; Isoflupredone Acetate; Isoxepac; Isoxicam; Ketoprofen; Lofemizole Hydrochloride; Lornoxicam; Loteprednol Etabonate; Meclofenamate Sodium; Meclofenamic Acid; Meclorisone Dibutyrate; Mefenamic Acid; Mesalamine; Meseclazone; Methylprednisolone Suleptanate; Momiflumate; Nabumetone; Naproxen; Naproxen Sodium; Naproxol; Nimazone; Olsalazine Sodium; Orgotein; Orpanoxin; Oxaprozin; Oxyphenbutazone; Paranyline Hydrochloride; Pentosan Polysulfate Sodium; Phenbutazone Sodium Glycerate; Pirfenidone; Piroxicam; Piroxicam Cinnamate; Piroxicam Olamine; Pirprofen; Prednazate; Prifelone; Prodolic Acid; Proquazone; Proxazole; Proxazole Citrate; Rimexolone; Romazarit; Salcolex; Salnacedin; Salsalate; Sanguinarium Chloride; Seclazone; Sermetacin; Sudoxicam; Sulindac; Suprofen; Talmetacin; Talniflumate; Talosalate; Tebufelone; Tenidap; Tenidap Sodium; Tenoxicam; Tesicam; Tesimide; Tetrydamine; Tiopinac; Tixocortol Pivalate; Tolmetin; Tolmetin Sodium; Triclonide; Triflumidate; Zidometacin; and Zomepirac Sodium.

In an embodiment, the CMBPC may contain additional ingredients as suitable for the formulation of a pharmaceutical composition. As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials.

Generally, the CMBPC may be administered systemically in dosage unit formulations containing conventional non-toxic pharmaceutically acceptable carriers, adjuvants, and vehicles as desired, or may be locally administered by means such as, but not limited to, injection, implantation, or grafting. In a specific embodiment, administration of the CMBPC may be by intravenous injection, endobronchial adminstration, intraaterial injection, intramuscular injection, intracardiac injection, subcutaneous injection, intraperitoneal injection, intraperitoneal infusion, transdermal diffusion, transmucosal diffusion, intracranial, intrathecal, or combinations thereof. A means of administering the CMBPC may include, but is not limited to, infusion. Systemically may also include, for example, by a pump, by an intravenous line, or by bolus injection. Bolus injection can include subcutaneous, intramuscular, or intraperitoneal routes.

Although the descriptions of pharmaceutical (e.g., CMBPC) and prophylactic compositions provided herein are principally directed to pharmaceutical compositions which are suitable for ethical administration to humans, it will be understood by the skilled artisan that such compositions are generally suitable for administration to animals of all sorts. Modification of compositions suitable for administration to humans of the type disclosed herein in order to render the compositions suitable for administration to various animals can be accomplished by the ordinarily skilled veterinary pharmacologist, with the benefit of this disclosure, who can design and perform such modifications with routine, if any, experimentation. Subjects to which administration of the pharmaceutical compositions of this disclosure is contemplated include, but are not limited to, humans and other primates; mammals including commercially relevant mammals such as cattle, pigs, horses, and sheep; companion animals such as cats, and dogs; and birds including commercially relevant birds such as chickens, ducks, geese, and turkeys.

In certain embodiments, a therapeutically effective dose of the CMBPC and/or RC is delivered to the subject. A therapeutically effective dose will be determined using a variety of factors (e.g., the body weight of the subject) and may be further modified, for example, based on the severity or phase of the medical condition. The number of cells in the CMBPC and/or RC used will depend on the weight and condition of the receiver subject, the number of or frequency of administrations, and other variables. For example, a therapeutic dose may be one or more administrations of the CMBPC and/or RC.

In an embodiment, the CMBPC and/or RC are formulated for topical administration into forms such as creams, lotions, serums, powders, ointments, or drops. A formulation of CMBPC and/or RC for topical administration may also contain pharmaceutically acceptable carriers, moisturizers, oils, fats, waxes, surfactants, thickening agents, antioxidants, viscosity stabilizers, chelating agents, buffers, preservatives, perfumes, dyestuffs, lower alkanols, humectants, emollients, dispersants, sunscreens such as radiation blocking compounds or UV-blockers, antibacterials, antifungals, disinfectants, vitamins, antibiotics, anti-acne agents, as well as other suitable materials that do not have a significant adverse effect on the activity of the topical composition. Nonlimiting exemplary pharmaceutically acceptable carriers that may be used in the compositions comprising the restored cells may include water, mixtures of water and water-miscible solvents such as lower alkanols or vegetable oils, and water-soluble ophthalmologically acceptable non-toxic polymers (for example, cellulose derivatives such as methylcellulose), glycerin, propylene glycol, methylparaben, alginates, glyceryl stearate, PEG-100 stearate, cetyl alcohol, propylparaben, butylparaben, sorbitols, polyethoxylated anhydrosorbitol monostearate (TWEEN®), white petrolatum (VASELINE®), triethanolamine, emu oil, aloe vera extract, lanolin, cocoa butter, LIPODERM® base, and the like. In an embodiment, the CMBPC and/or RC formulated for topical administration may be applied to one or more areas of the skin including the face, hands, and neck.

In an embodiment, the methodologies disclosed herein result in therapies that are prophylactic, palliative, curative, or combinations thereof. Methodologies and compositions of the type disclosed herein may be utilized in the treatment of a wide variety of medical conditions related to decreases in cellular function and viability such as age-related medical conditions that include neurological disorders; autoimmune diseases; and disorders associated with radiation overexposure (chronic or acute).

It is contemplated the methodologies and compositions disclosed herein may result in an increased expression of genes associated with improved cellular health with a concomitant decrease in the expression of genes associated with adverse cellular events. In some embodiments, the methodologies and compositions disclosed herein result in an increased expression of genes associated with beneficial cellular events.

According to another aspect of the disclosure, kits are provided. Kits, according to the present disclosure, include package(s) or containers comprising the compositions disclosed herein (e.g., RC, cell-free culture media) and may include defined culture medium and cell culture medium supplement. The kit may further include an instruction letter or package-associated instruction for the treatment and/or prophylaxis of a medical condition. The phrase "package" means any vessel containing the compositions (including stem cells, media, and/or media supplement) presented herein. For example, the package can be a box or wrapping. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. The kit can also contain items that are not contained within the package but are attached to the outside of the package, for example, pipettes. Kits may optionally contain instructions for administering compositions of the present disclosure to a subject having a condition in need of treatment. Kits may also comprise instructions for approved uses of compounds herein by regulatory agencies, such as the United States Food and Drug Administration. Kits may optionally contain labeling or product inserts for the present compositions. The package(s) and/or any product insert(s) may themselves be approved by regulatory agencies. The kits can include compounds in the solid phase or in a liquid phase (such as buffers provided) in a package. The kits also can include buffers for preparing solutions for conducting the methods, and pipettes for transferring liquids from one container to another. The kit may optionally also contain one or more other compounds for use in combination therapies as described herein. In certain embodiments, the package(s) is a container for intravenous administration.

In an embodiment, a subject having undergone a restoration method of the type disclosed herein may be subsequently monitored for some time period. Monitoring of the subject may comprise qualitative and quantitative evaluations of the subject's general health and/or medical condition. In some embodiments, a subject may be subjected to a plurality of cellular restoration methods of the type disclosed herein. For example, a receiver subject having undergone a cellular restoration method of the type disclosed herein may display quantitative and/or qualitative improvements in the subject's general health and/or medical condition for some time period. Subsequently, the receiver subject may experience some decline in their general health and/or medical condition and another cellular restoration process may be carried out. The cellular restoration process may involve obtaining a donor cell sample and/or receiver cell sample utilizing the methodologies disclosed herein, performing cellular restoration of the receiver cell sample and administering the restored cell sample to the receiver subject. Alternatively, the receiver subject may be administered at least a portion of the restored cell sample remaining from a prior cellular restoration process.

In some embodiments, evaluations of the subject comprise determinations based on analyses disclosed herein (e.g., natural killer assay, telomere length, gene and protein biomarker arrays). In such embodiments, the subject may provide a receiver cell sample and the quality of the sample evaluated as disclosed herein. In some embodiments, the receiver cell sample quality value at some point post-restoration may be compared to the receiver cell sample quality value pre-restoration and this information utilized to assess whether additional treatment is needed. For example, a subject having a receiver cell sample pre-restoration quality value of 5 may have a receiver cell sample post-restoration quality value of 9 for a time period of up to about 1 year subsequent to the restoration process. The subject's post-restoration receiver cell sample quality value after 1.5 years may have decreased to 7 while after 3 years the value may be 5. In such instances, the subject may be administered another RC.

In an embodiment, a method for cellular restoration comprises the isolation of one or more constituents present in the culture media of a donor cell sample. Such materials may be investigated for their ability to restore cellular functions of the type disclosed herein to a receiver cell sample. In an embodiment, the IREs comprise vesicular bodies or materials derived from vesicular bodies such as exosomes, exosome complexes, proteins, cytokines, microvesicles, microvesicle complexes, microRNAs, large non-coding RNAs or combinations thereof. Exosomes are composed of an evolutionary-conserved common set of protein molecules that vary with the cell and tissue of origin, as well as mRNA and non-coding RNA (ncRNA) molecules, such as microRNA (miRNA) and long non-coding RNA (lncRNA). Exosomes function as mediators of extracellular signaling, via the membrane-protected transfer of cellular material and may play a variety of roles such as induction of tolerance against allergen, eradication of established tumors in mice, and the inhibition and activation of natural killer cells. As will be understood by one of ordinary skill in the art, exosomes and microvesicles can be envisioned as carriers of biomolecule cargo (e.g, RNA, proteins). Hereinafter, for simplicity, carriers isolated from a donor cell sample with the ability to restore cellular functions of the type disclosed herein to a receiver cell sample (e.g., exosomes) are termed collectively termed isolated restoring elements (IRE) while the cargo present in such IREs (e.g., RNA) are collectively termed molecules of cellular restoration (MCR).

IREs may be identified from the culture media (CM) of a donor cell sample using any suitable methodology. For example, IREs may be isolated from CM through either ultracentrifugation or precipitation/low speed centrifugation with commercially available products such as exosome isolation kits.

In an embodiment, the IRE is a microvesicle also known as microparticles or ectosomes. Microvesicles are fragments of plasma membranes that are usually larger than 0.2 µm in size which are shed from all cell types. Microvesicles also play a role in intracellular communication and can transport mRNA, miRNA, proteins, and lipids between cells. In an embodiment, an RC of the type disclosed herein is a mixture comprising isolated exosomes and a pharmaceutically acceptable carrier formulated for administration to a subject. In an embodiment, an RC of the type disclosed herein is a mixture comprising isolated microvesicles and a pharmaceutically acceptable carrier formulated for administration to a subject.

In an embodiment, isolated exosomes and/or isolated microvesicles may be utilized in the compositions and methodologies disclosed herein. Alternatively, isolated exosomes and/or isolated microvesicles may be further subjected to methodologies to isolate and/or characterize materials associated with the exosomes and/or microvesicles.

In an embodiment, the methods disclosed herein further comprise analysis of the cargo (i.e., biochemical composition) of the isolated exosomes and/or microvesicle (i.e., MCR). Any suitable methodology may be employed for determining the biochemical composition of the exosomes and/or microvesicles. For example, exosomal or microvesical material may be extracted and the extracted material subjected to characterization by techniques such as sequencing and gel analysis. Isolated exosomal and/or microvesical material may be investigated to determine the ability of these materials to effect cellular restoration in a manner similar to those disclosed previously herein for the RCs. In an embodiment one or more constituents of the biochemical composition of an isolated exosome and/or microvesicle are determined to effect the cellular restoration of a receiver cell sample.

In an embodiment, an MCR of the type disclosed herein may comprise isolated macromolecules such as proteins, genomic DNA (gDNA), mitochondrial DNA (mtDNA, major histocompatibility complex (MHC), polysaccharides, cytokines, lipids, nucleic acids, RNA, or combinations thereof. Alternatively, an MCR of the type disclosed herein may comprise a small molecule such as a metabolite, or natural product. In an embodiment, the MCR may be sourced from cellular material (e.g., a donor cell sample). Alternatively, the MCR may be recombinant in nature in the case of macromolecules or may be synthetic in the case of small molecules. An embodiment of a composition suitable for use in the present disclosure comprises an MCR formulated for administration to a subject in need thereof. Such materials may be administered in a manner similar to those disclosed for administration of one or more embodiments of RCs. For example, a formulation suitable for administration to a subject in need thereof may comprise an IRE and/or MCR and one or more of the pharmaceutically active materials disclosed herein (e.g., antibiotics).

IREs and/or MCRs for parenteral injection may comprise pharmaceutically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity may be maintained, for example, by the use of a coating such as lecithin, by the maintenance of the required particle size in the case of dispersions, and by the use of surfactants.

Compositions comprising the IREs and/or MCRs may also contain pharmaceutically acceptable carriers, moisturizers, oils, fats, waxes, surfactants, thickening agents, antioxidants, viscosity stabilizers, chelating agents, buffers, preservatives, perfumes, dyestuffs, lower alkanols, humectants, emollients, dispersants, sunscreens such as radiation blocking compounds or UV-blockers, antibacterials, antifungals, disinfectants, vitamins, antibiotics, anti-acne agents, as well as other suitable materials that do not have a significant adverse effect on the activity of the topical composition. Nonlimiting exemplary pharmaceutically acceptable carriers that may be used in the compositions comprising the IRE may include water, mixtures of water and water-miscible solvents such as lower alkanols or vegetable oils, and water-soluble ophthalmologically acceptable non-toxic polymers (for example, cellulose derivatives such as methylcellulose), glycerin, propylene glycol, methylparaben, alginates, glyceryl stearate, PEG-100 stearate, cetyl alcohol, propylparaben, butylparaben, sorbitols, polyethoxylated anhydrosorbitol monostearate (TWEEN), white petrolatum (VASELINE), triethanolamine, emu oil, aloe vera extract, lanolin, cocoa butter, LIPODERM base, and the like.

Prevention of the action of microorganisms may be effected by the inclusion by various antibacterial and antifungal agents in any of the compositions disclosed herein for example, parabens, chlorobutanol, phenol, sorbic acid, and the like. It may also be desirable to include isotonic agents, for example, sugars, sodium chloride and the like.

In an embodiment, the IREs and/or MCRs are formulated as compositions for topical administration. Such topical restoring compositions may include additives suitable for the formulation of a composition for topical application. In an embodiment, the topical restoring composition may be applied to one or more areas of the skin including the face, hands and neck.

EXAMPLES

The subject matter of the present disclosure having been generally described, the following examples are given as particular embodiments of the disclosure and to demonstrate the practice and advantages thereof. It is understood that the examples are given by way of illustration and are not intended to limit the specification or the claims to follow in any manner.

Example 1

Sample and Techniques

Peripheral blood mononuclear cells were collected from subjects having undergone a Stage B preparation involving the administration of the mobilizer NEUPOGEN® (filagrastim). For the following experiments peripheral blood mononuclear cells (1×5 mL vial per subject) were found to contain the following number of nucleated cells:

| Subject | Approximate Age | Sex | Cell Number |
|---|---|---|---|
| R1 | 70 | Male | $1.8 \times 10^8$ |
| R2 | 70 | Male | $2.7 \times 10^8$ |
| R3 | 60 | Male | $2.2 \times 10^8$ |
| D1 | 26 | Male | $3.3 \times 10^8$ |
| D2 | 30 | Male | $1.8 \times 10^8$ |
| D3 | 28 | Female | $1.9 \times 10^8$ |

The cells following harvest were cryopreserved and upon thawing were determined by trypan blue dye exclusion and flow cytometry to be greater than 95%.

The percentages of stem cell, progenitor cell and mature cell populations were determined by flow cytometry. Table 3 shows the average percentage of hematopoietic stem cells (HSCs) and early hematopoietic progenitor cells (HPCs) to be ~0.5% and 1.0% respectively of the total mobilized cell collection.

TABLE 3

| | Hematopoietic Cells $CD45^+$ | Hematopoietic Stem Cells $CD34^+$ $CD38^-$ | Hematopoietic Progenitor Cells $CD34^+$ $CD38^+$ | T Cells $CD3^+$ | NK Cells $CD56^+$ |
|---|---|---|---|---|---|
| % Total Cell Population | | | | | |
| R1 | 64.4 | 0.5 | 0.3 | 39.6 | 4.2 |
| R2 | 59.9 | 0.4 | 1.6 | 29.7 | 7.5 |
| R3 | 86.3 | 0.4 | 0.3 | 56.7 | 2.9 |
| D1 | 64.0 | 1.0 | 1.5 | 32.4 | 5.7 |
| D2 | 59.9 | 0.3 | 0.8 | 36.0 | 4.1 |
| D3 | 59.0 | 4.1 | 1.0 | 10.5 | 5.5 |
| % Hematopoietic ($CD45^+$) Population | | | | | |
| R1 | 100 | 0.7 | 0.4 | 61.5 | 6.5 |
| R2 | 100 | 0.7 | 2.8 | 49.5 | 12.5 |
| R3 | 100 | 0.4 | 0.4 | 65.7 | 3.4 |
| D1 | 100 | 1.5 | 2.4 | 50.5 | 8.9 |
| D2 | 100 | 0.5 | 1.3 | 60.1 | 6.9 |
| D3 | 100 | 7.0 | 1.7 | 51.7 | 9.3 |

TABLE 4

| | Non-Hematopoietic Cells $CD45^-$ | Mesenchymal Stem Cells $CD29^+$ $CD44^+$ $CD105^+$ | Endothelial Progenitor Cells $CD31^+$ $CD105^+$ |
|---|---|---|---|
| % Total Cell Population | | | |
| R1 | 17.9 | 0.11 | 0.06 |
| R2 | 38.7 | 0.91 | 0.79 |
| R3 | 11.1 | 0.22 | 0.18 |
| D1 | 33.4 | 0.52 | 0.44 |

TABLE 4-continued

|  | Non-Hematopoietic Cells CD45⁻ | Mesenchymal Stem Cells CD29⁺ CD44⁺ CD105⁺ | Endothelial Progenitor Cells CD31⁺ CD105⁺ |
| --- | --- | --- | --- |
| D2 | 26.7 | 0.69 | 0.65 |
| D3 | 40.4 | 0.63 | 0.46 |
| % Non-Hematopoietic (CD45⁻) Population | | | |
| R1 | 100 | 0.60 | 0.35 |
| R2 | 100 | 2.34 | 2.05 |
| R3 | 100 | 1.94 | 1.58 |
| D1 | 100 | 1.57 | 1.32 |
| D2 | 100 | 2.57 | 2.43 |
| D3 | 100 | 1.56 | 1.14 |

Receiver cell samples (i.e., R1, R2, and R3) were individually paired with donor cell samples (i.e., D1, D2, and D3) and the pairs co-cultured in a transwell culture cell for four weeks. The morphology of the cells was studied at 2 weeks into the co-culture and at 4 weeks of co-culture. Gene expression arrays, protein arrays, and telomere length experiments compared freshly defrosted cells from the collection tubes (referred to as the baseline donor cell sample or baseline receiver cell sample) with cells at the 4-week study endpoint (referred to as restored cell samples).

At the midpoint of the co-culture (i.e., 2 weeks) baseline receiver cell samples displayed morphologies consistent with low viability. Restored cell samples displayed a robust cellular morphology that included colony formation.

Example 2

Protein array analyses were carried out using conditioned media from the baseline donor cell sample or baseline receiver cell sample. The conditioned media was mixed with like cellular protein extracts and applied to the custom-designed arrays which consisted of antibody probes for 68 factors linked to cellular aging and senescence, collectively referred to as the senescence-associated secretory factors (SASF). Quantitative PCR gene array analyses were carried out by extracting RNA from the baseline samples or the co-cultured donor and receiver samples. The data presented represents the average metric determined for either the baseline donor cell sample, the baseline receiver cell sample, or the restored cell sample.

Figure 3:
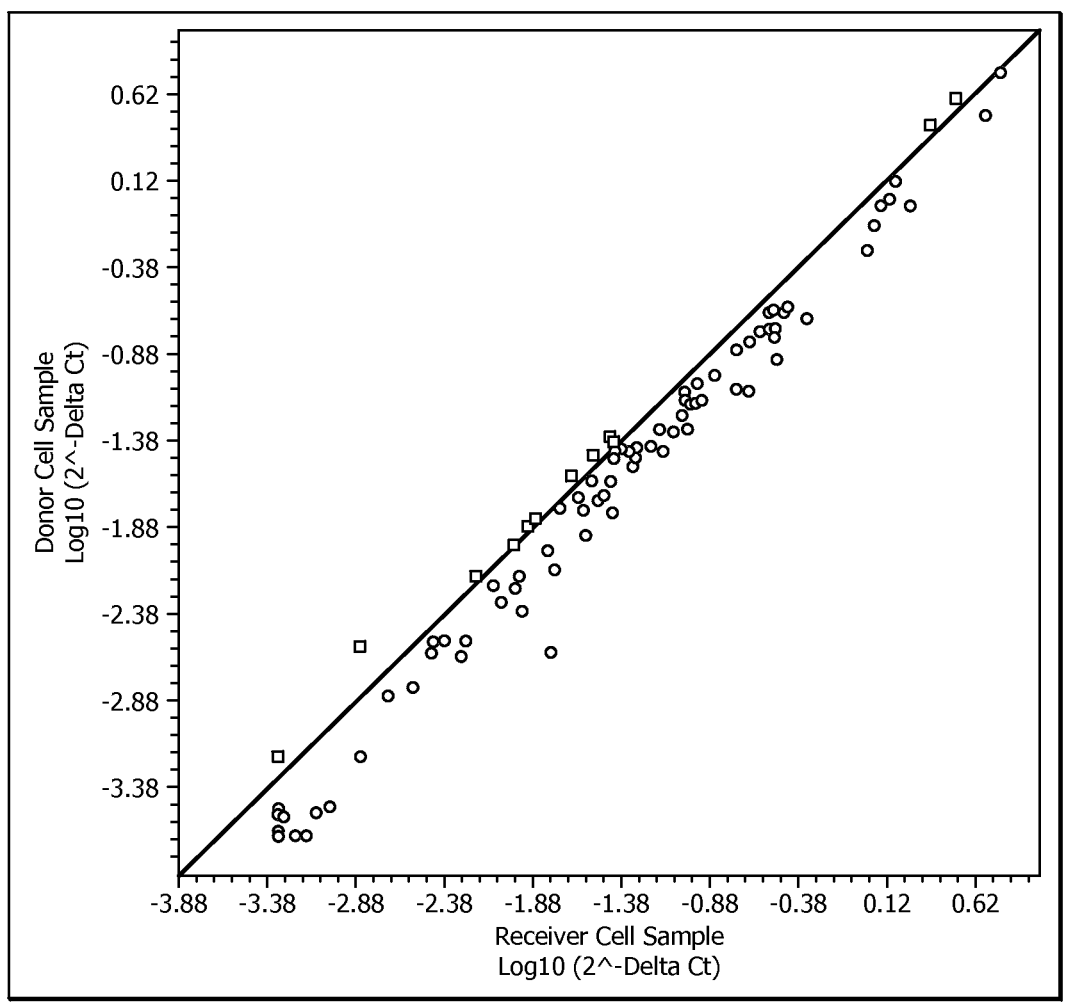
FIG. 3 is a plot of a gene expression analysis for donor cell samples and receiver cell samples.
Figure 4:
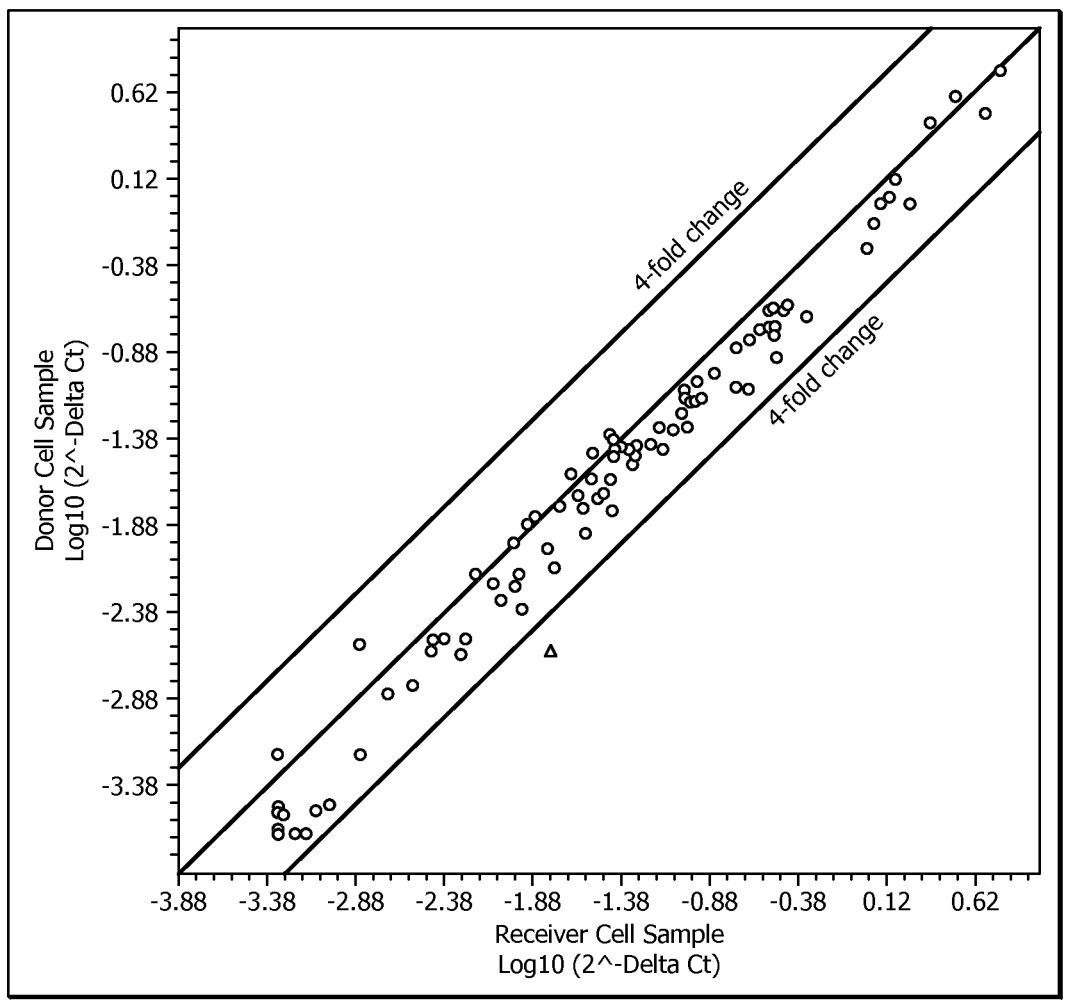
FIG. 4 is a plot of a protein expression analysis for donor cell samples and receiver cell samples.
Figure 5A:
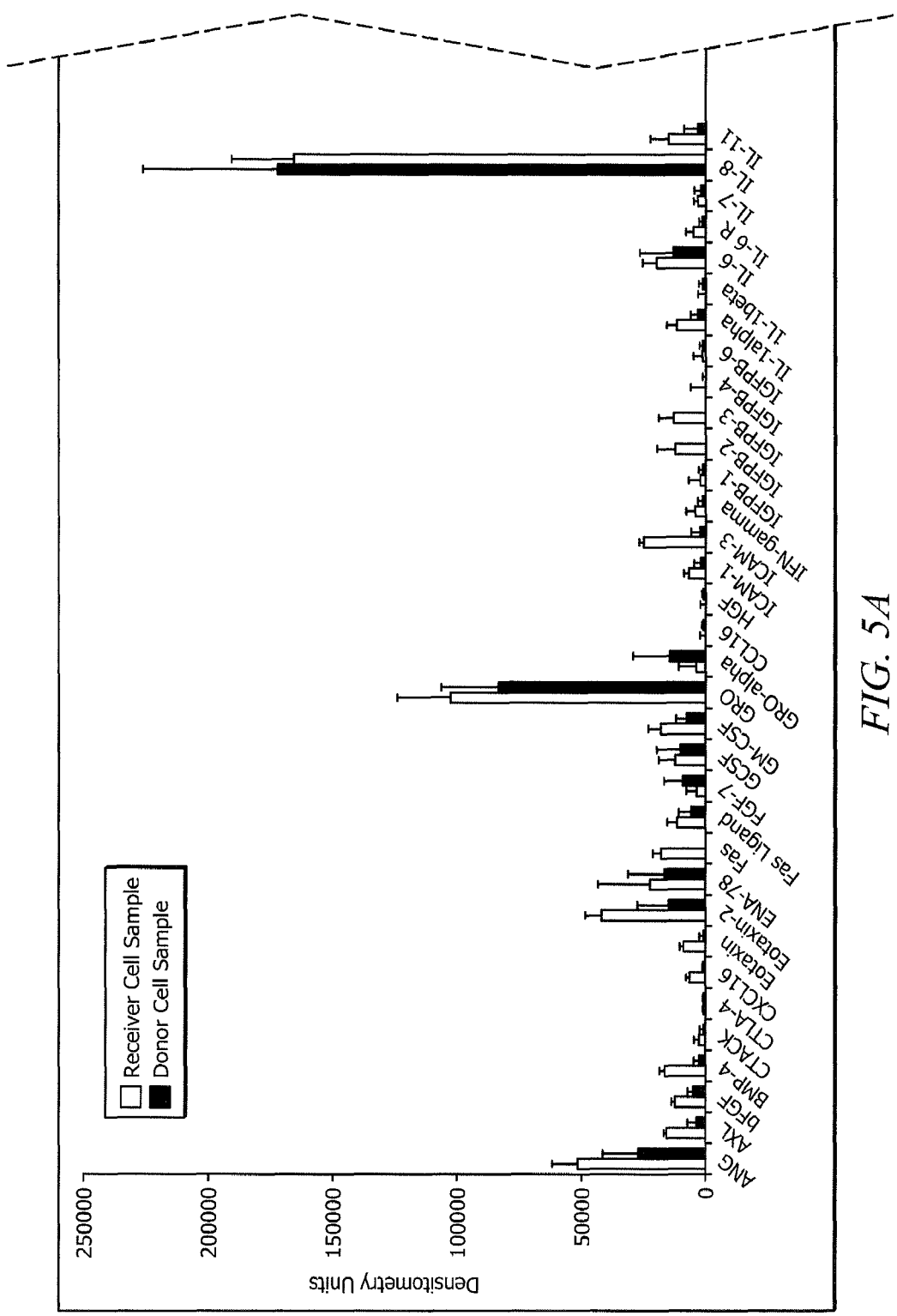
FIGS. 5A and 5B are a plot of a level of expression of the indicated proteins for the donor cell samples and receiver cell samples.
Figure 5B:
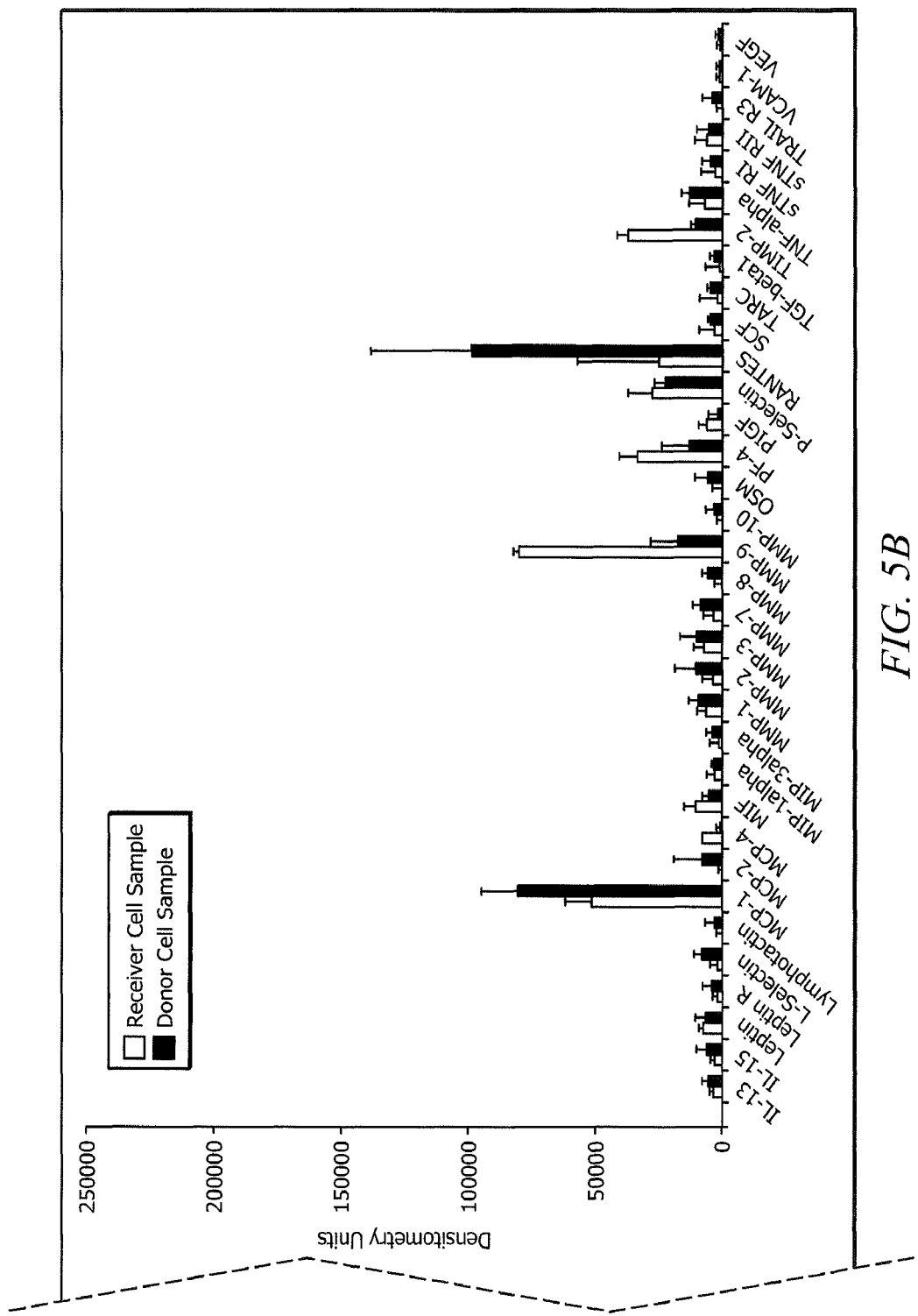
Figure 6:
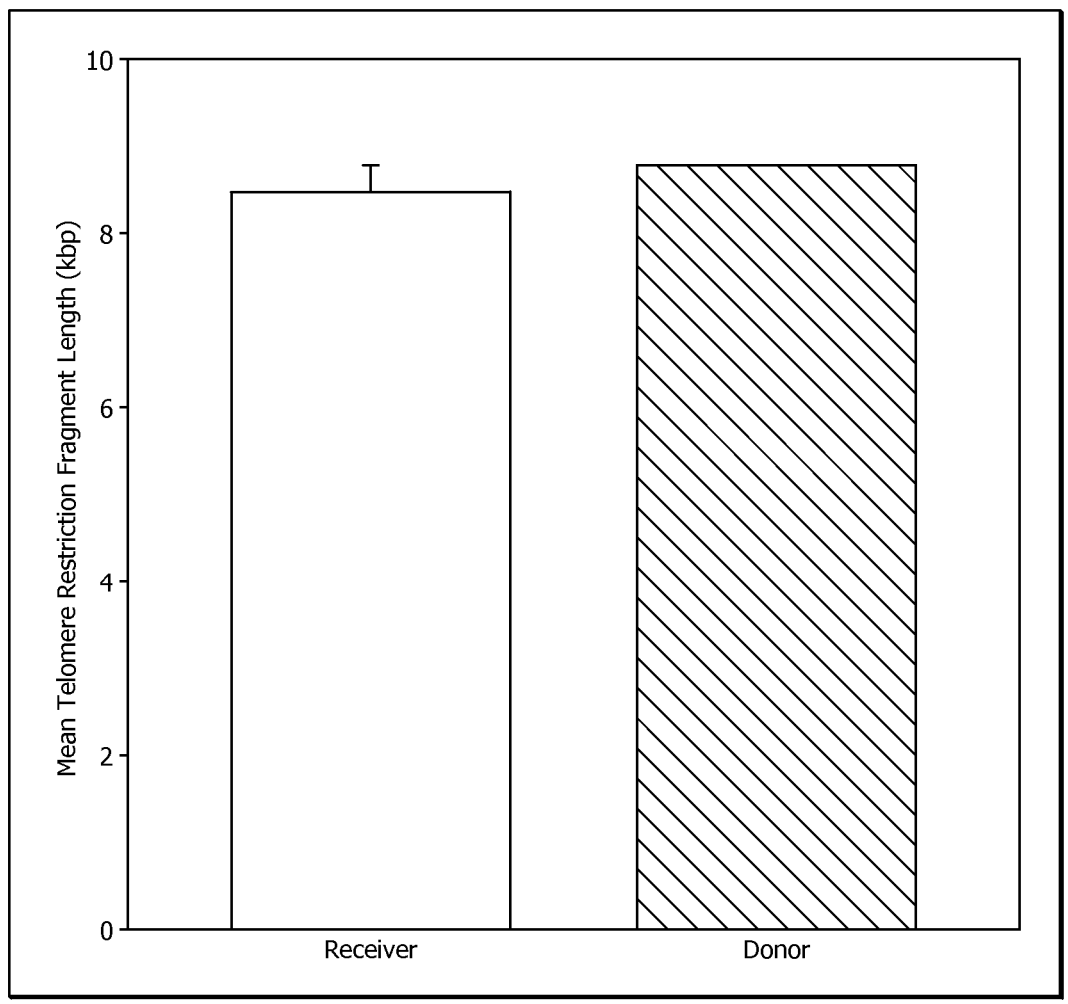
FIG. 6 is a plot of the average telomere length for the donor cell samples and receiver cell samples.

The results of the gene array analyses demonstrated that there was less than a 2-fold difference in the majority of senescence-related genes for the baseline donor cell samples and the baseline receiver cell samples, FIGS. 3 and 4. In all of the figures presented as plots of the gene expression analysis, the squares represent genes which are expressed at a lower level following the cellular restoration, triangles represent genes expressed at a higher level following restoration and circles represent genes whose expression level was determined to be substantially similar to the expression level prior to cellular restoration. The designation of "substantially similar" is qualitative and reflects the close proximity of the value to the line. The data suggests the techniques disclosed herein for the mobilization and collection of donor cell samples and receiver cell samples select for non-senescent cells. The results of the protein-based arrays, which assessed levels of senescence-related factors produced either within the cells or released into the culture media, similarly displayed little difference between the senescence-related factors among the donor cell sample and receiver cell sample, FIG. 5. The mean telomere length between the donor cell samples and receiver cell samples were not found to be significantly different, FIG. 6.

The results demonstrate that the gene expression profiles and protein expression profiles of the donor cell samples and receiver cell samples were similar despite the difference in age of the subjects. Further, despite the difference in age between the donor subjects and receiver subjects, the cells had similar telomere lengths.

Example 3

Figure 7:
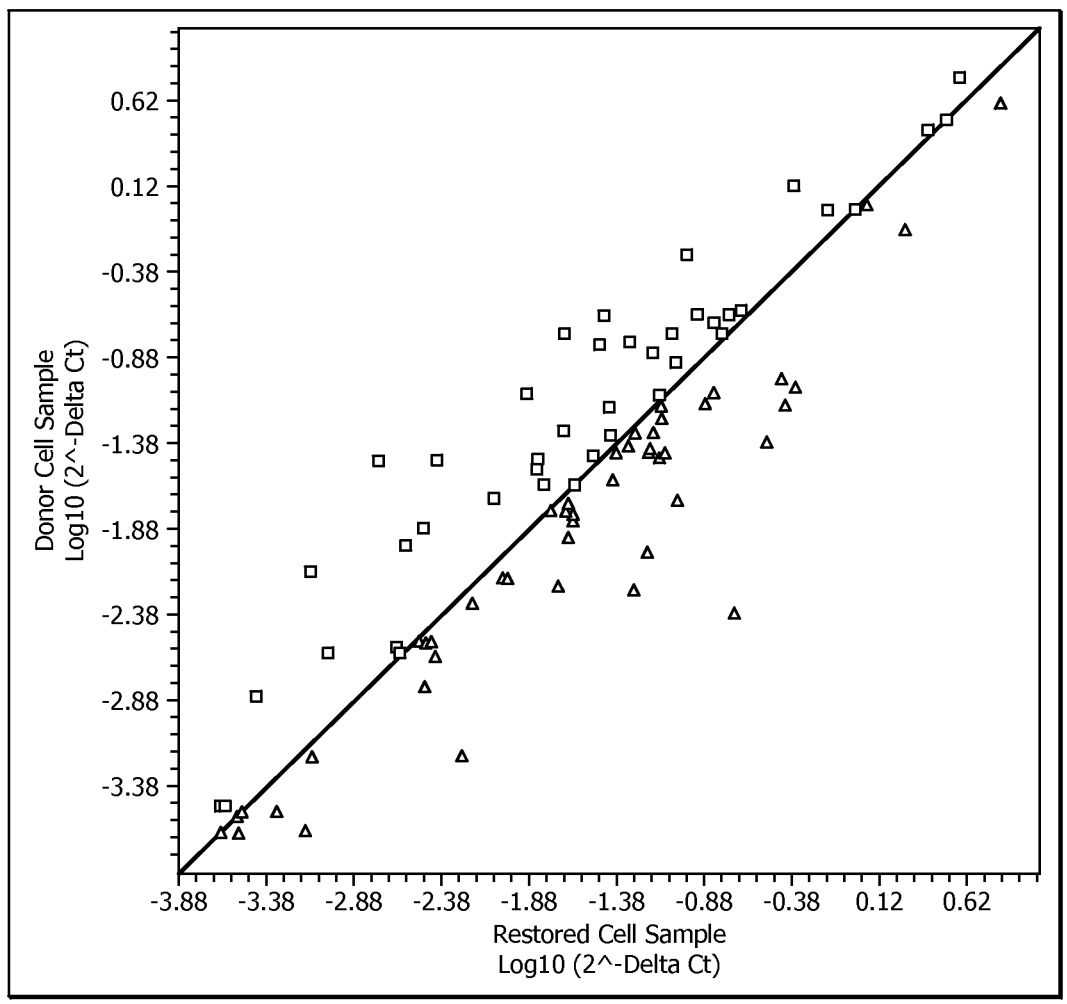
FIG. 7 is a plot of a gene expression analysis for baseline donor cell samples and restored cell samples.
Figure 8:
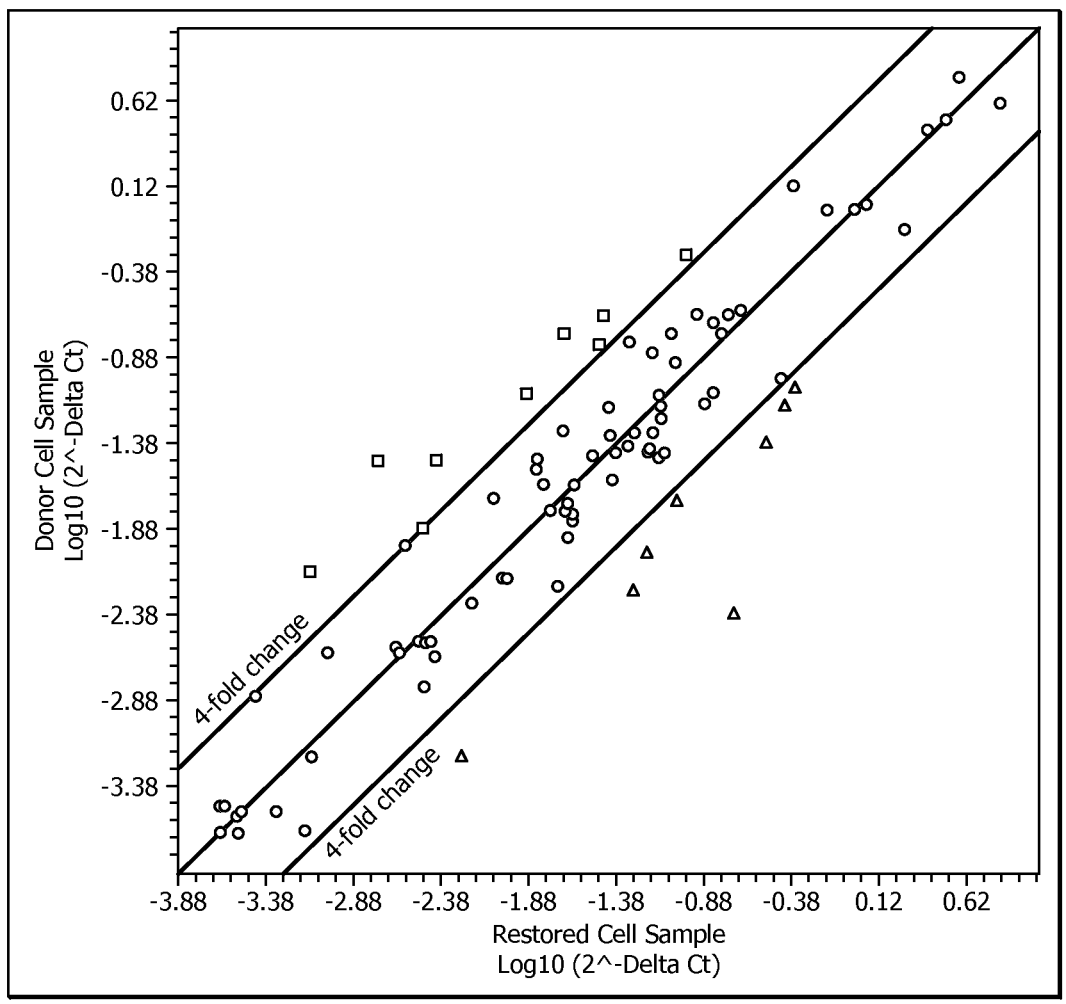
FIG. 8 is a plot of a protein expression analysis for baseline donor cell samples and restored cell samples.

The restored cell samples were investigated using the gene and protein arrays of Example 2 and are shown in FIGS. 7 and 8, respectively. For each of the restored cell samples investigated, approximately half of the examined genes (as designated by the "Xs" on the Figure) were expressed at a lower level in the restored cell samples when compared to the baseline donor cell sample. The genes that were expressed at a lower level were genes associated with improving cellular function and decreasing the extent of cellular senescence and aging. The data suggests the gene expression profile of the restored cell samples were altered by the transwell restoration and more closely approximated that of the baseline donor cell sample than that of the baseline receiver cell sample. The data demonstrate the restore cell sample exhibited a decreased expression of senescence-related genes of receiver cells and/or cell types compared to the receiver cell sample, wherein senescence-related genes are defined as the RBGEP, by quantitative polymerase chain reaction as shown in FIGS. 7 and 8.

Figure 9A:
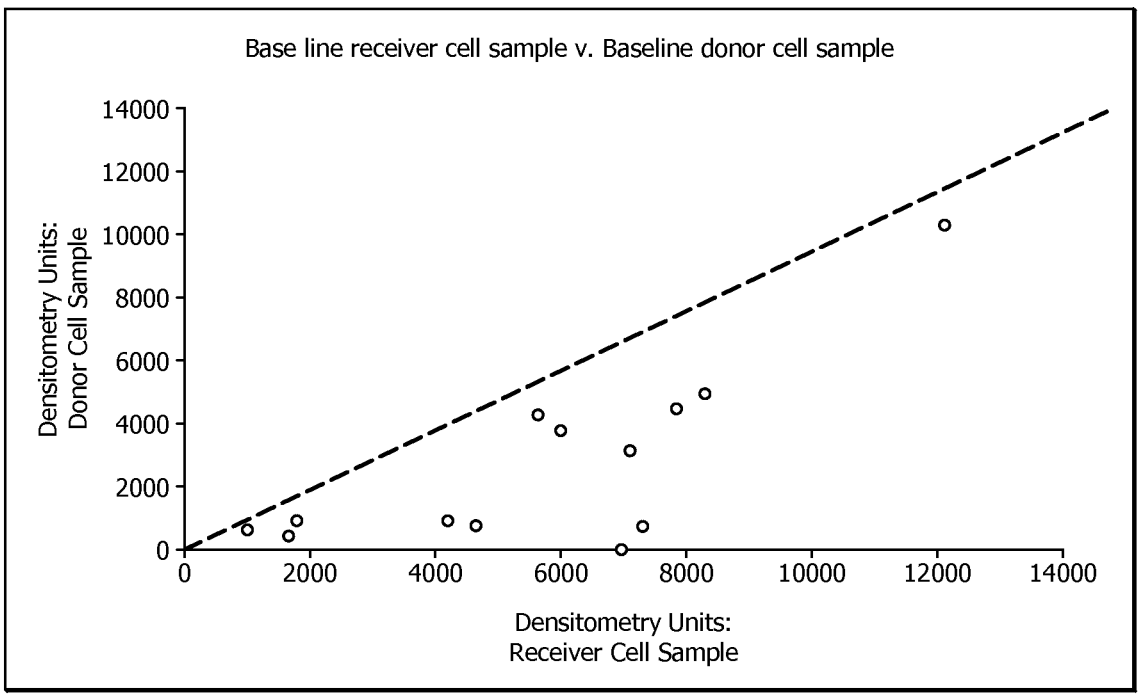
FIG. 9A is a plot of a protein expression analysis for baseline donor cell samples and baseline receiver cell samples.
Figure 9B:
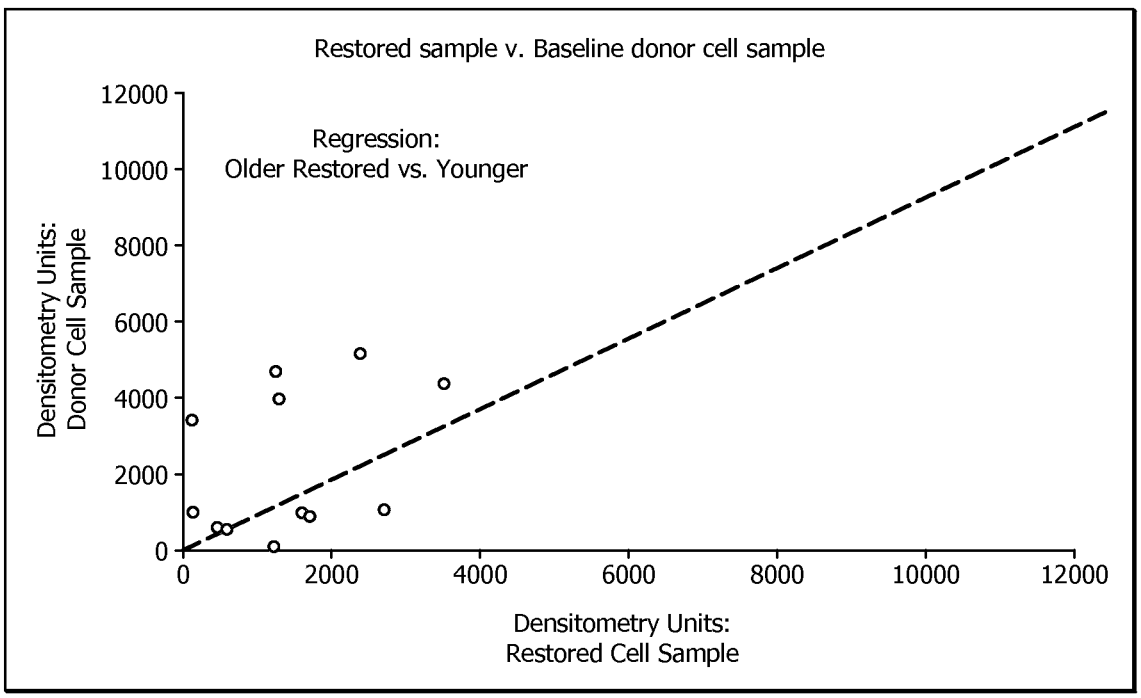
FIG. 9B is a plot of a protein expression analysis for baseline donor cell samples and baseline donor cell samples and restored cell samples.
Figure 10A:
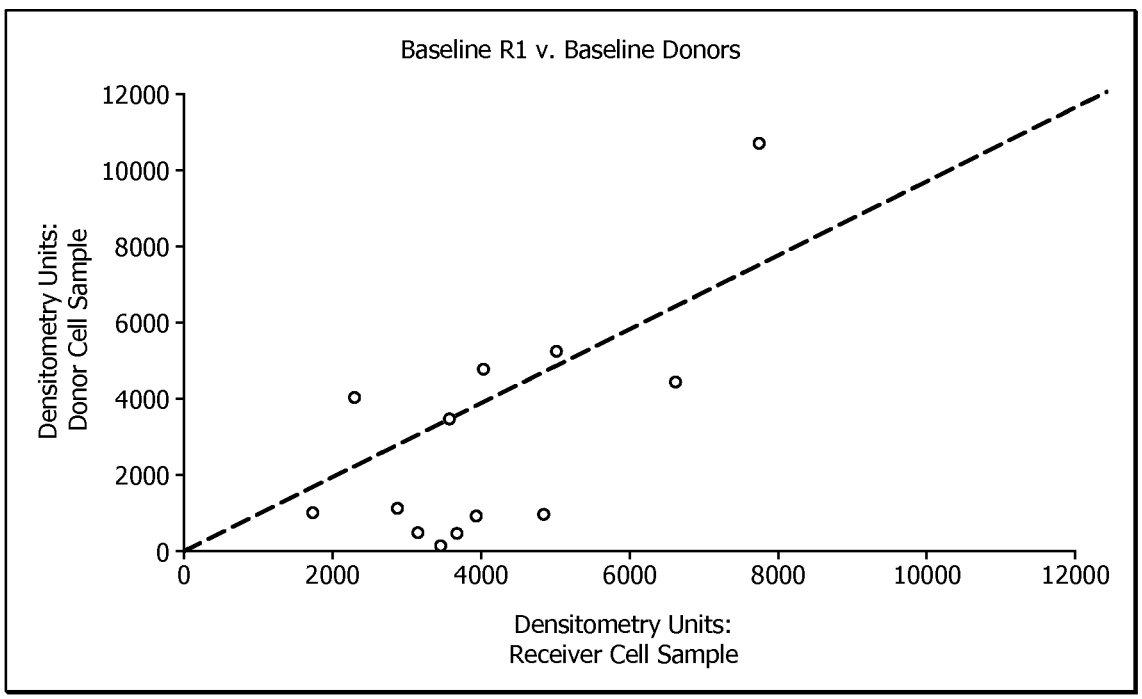
FIG. 10A is a plot of a protein expression analysis for the baseline donor cell sample and the baseline receiver cell sample R1.
Figure 10B:
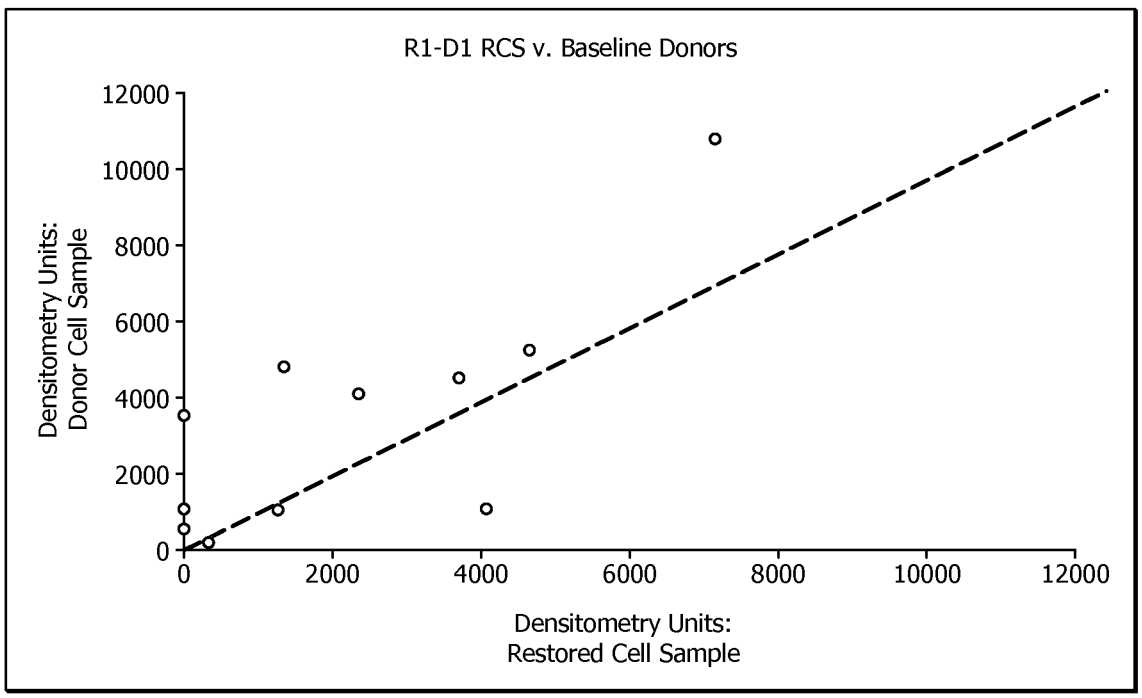
FIG. 10B is a plot of a protein expression analysis for the baseline donor cell sample and restored cell sample R1-D1.
Figure 10C:
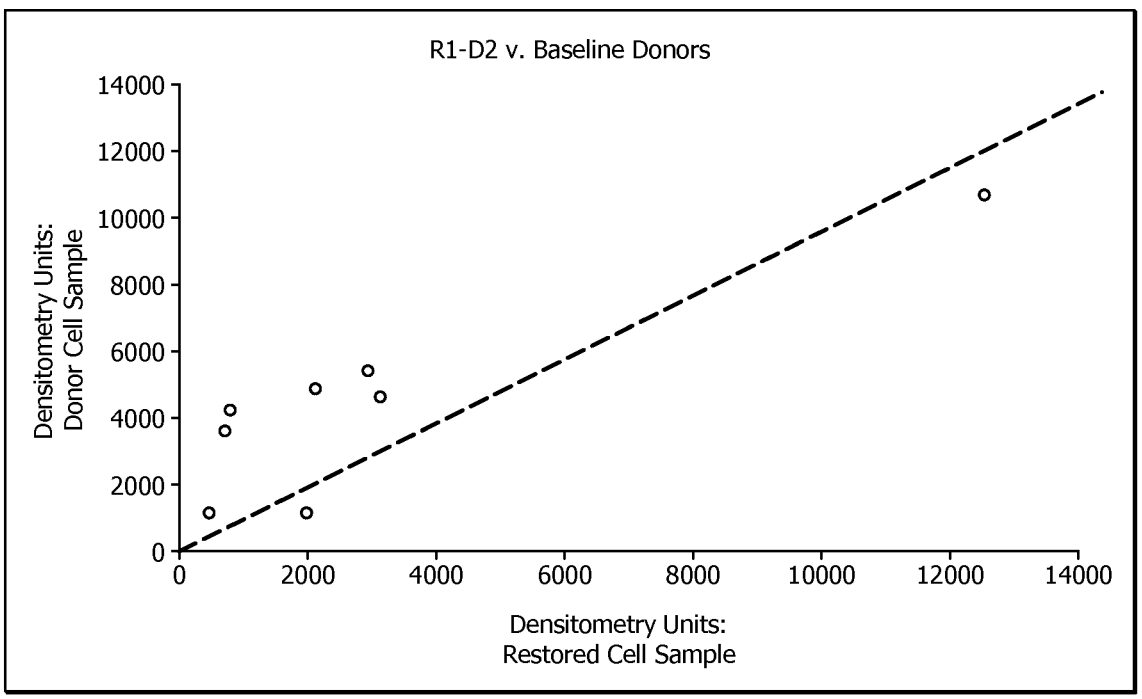
FIG. 10C is a plot of a protein expression analysis for the baseline donor cell sample and restored cell sample R1-D2.
Figure 10D:
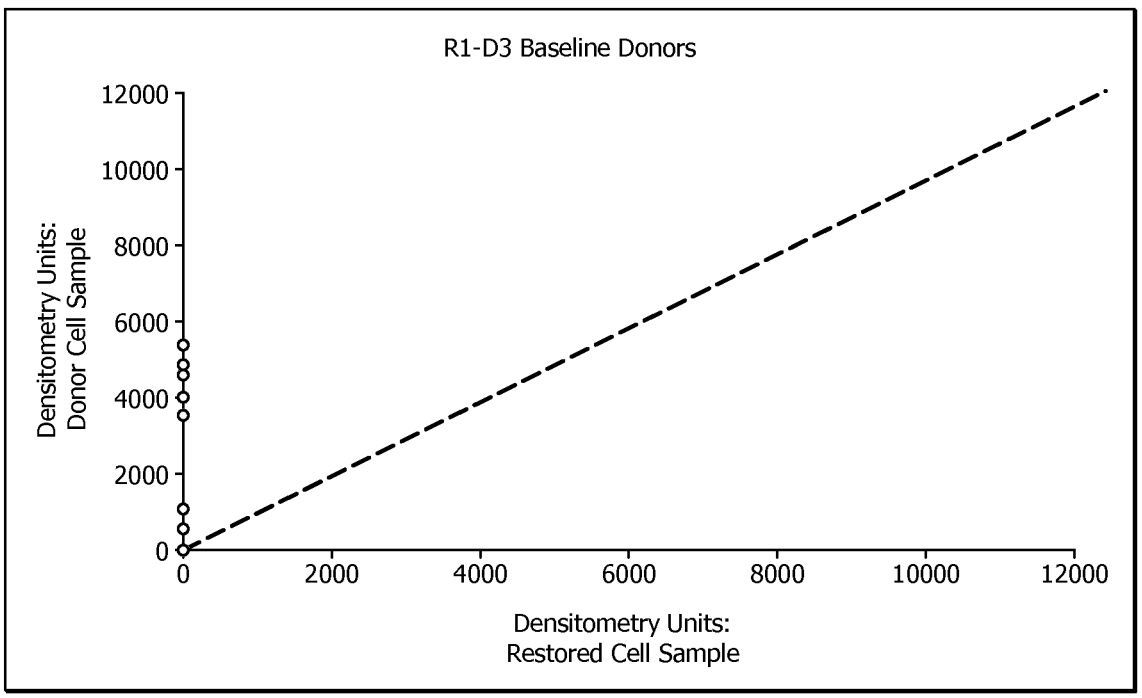
FIG. 10D is a plot of a protein expression analysis for the baseline donor cell sample and restored cell sample R1-D3.
Figure 11:
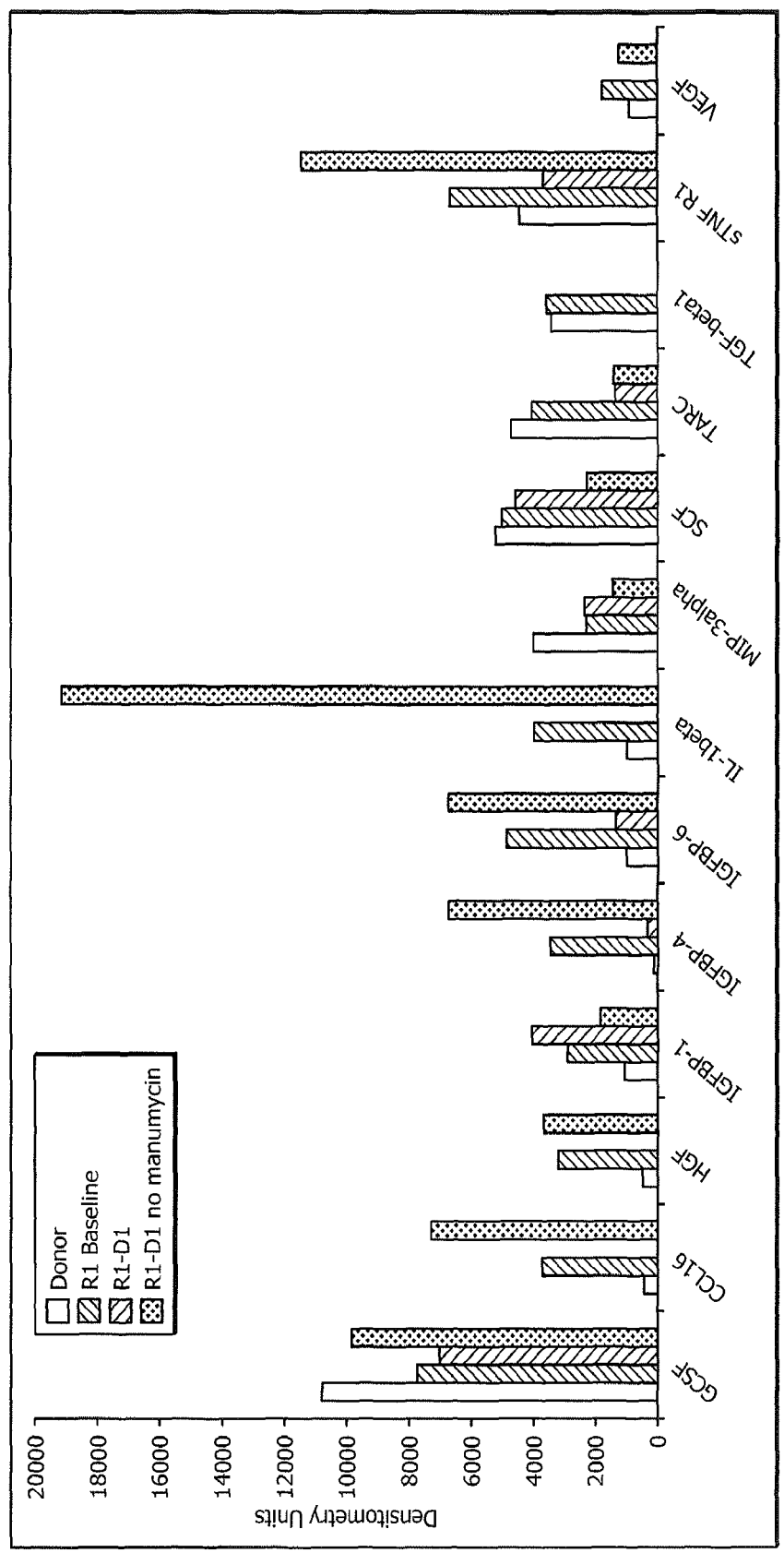
FIG. 11 is a plot of a level of protein expression in restored cells in the presence or absence of manumycin.

Further, examination of the clustering analyses revealed a subset of genes (designated gene set A) whose expression was consistently elevated in the baseline receiver cell sample but whose expression was reduced in the restored cell sample. The expression of Gene Set A in the restored cell sample was reduced to levels comparable to those observed in the baseline donor cell sample. Similarly, as shown in FIG. 9A, stratification of the protein arrays identified 13 factors that showed a similar elevated trend in the baseline receiver cell samples when compared to that of the baseline donor cell samples. Likewise, as shown in FIG. 9B, the restored cell samples exhibit a level of expression of the identified 13 factors comparable to that observed in the baseline donor samples. These findings demonstrate a methodology for monitoring the restoration of the receiver cell sample by gene and protein array analyses. Further, these data demonstrate the restored cell sample exhibited a decreased expression of senescence-associated secretory factors compared to the receiver cell sample at baseline, wherein senescence-associated secretory factors are defined in Table 1, as measured by antibody array, as in FIGS. 9, 10 and 11, or enzyme-linked immunosorbant assay.

Example 4

Gene and protein arrays of restored cell samples for individual pairs of baseline donor cell samples and receiver cell samples were investigated. Specifically receiver cell sample R1 was co-cultured in a transwell experiment with donor cell samples from D1 (FIG. 10B), D2 (FIG. 10C), and D3 (FIG. 10D) respectively. Hierarchical clustergrams showed that all of the genes investigated are elevated in the receiver cell sample (FIG. 10A) while these same genes are expressed at low to modest levels in D1, D2 and D3. The restored cell sample was found to have a gene expression comparable to that of the level of expression observed for D1, D2, and D3. Experiments carried out using receiver cell samples R2 or R3 with donor cell samples D1, D2, or D3 exhibited similar results.

Example 5

Figure 12:
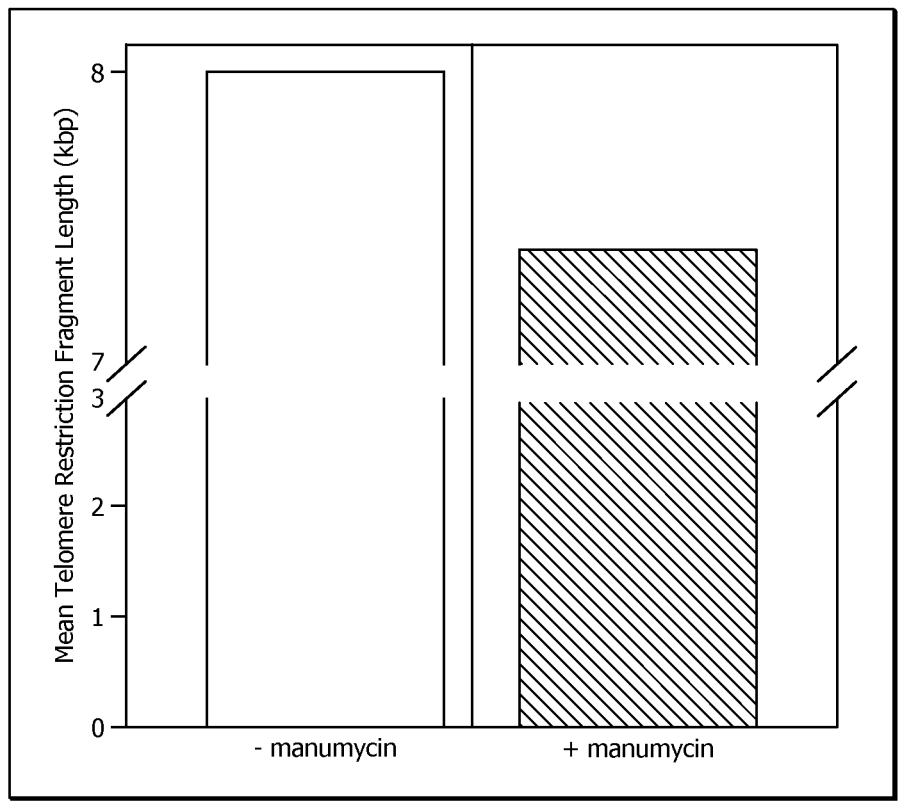
FIG. 12 is a plot of the telomere length for the restored cell sample from the donor cell sample-receiver cell sample pair R1-D1 in the presence or absence of manumycin.

The nature of the soluble particles passing through the permeable membrane in the transwell co-culture experiments was investigated. Specifically, transwell co-culture experiments were carried out in the presence or absence of manumycin. Manumycin, -[(1S,5S,6R)-5-hydroxy-5-[(1E,3E,5E)-7-[(2-hydroxy-5-oxo-1-cyclopenten-1-yl)amino]-7-oxo-1,3,5-heptatrien-1-yl]-2-oxo-7-oxabicyclo[4.1.0]hept-3-en-3-yl]-2E,4E,6R-trimethyl, 2,4-decadienamide, is an antibiotic that acts a potent and selective farnesytransferase inhibitor. Mannumycin is also known to inhibit the release of exosomes. Restored cells co-cultured in the presence of 5 µM manumycin displayed less robust morphology than restored cells cultured in the absence of manumycin. Gene expression analysis of restored cell samples co-cultured in the presence of manumycin did not display a change in expression levels similar to those observed in the absence of manumycin. In contrast, protein expression analyses of restored cell samples co-cultured in the presence of manumycin found elevated levels of all proteins investigated when compared to the proteins levels for restored cell samples co-cultured in the absence of manumycin, FIG. 11. The data suggests the role of exosome/microvesicles in mediating the disclosed cellular restoration process. Further support for the role of exosome/microvesicles in mediating the disclosed cellular restoration process is shown in FIG. 12. FIG. 12 displays the telomere length for a restored cell sample co-cultured in the presence or absence of manumycin. The telomere length in the presence of manumycin is decreased suggesting exosome/microvesicles play a role in the restoration process.

Example 6

Figure 13:
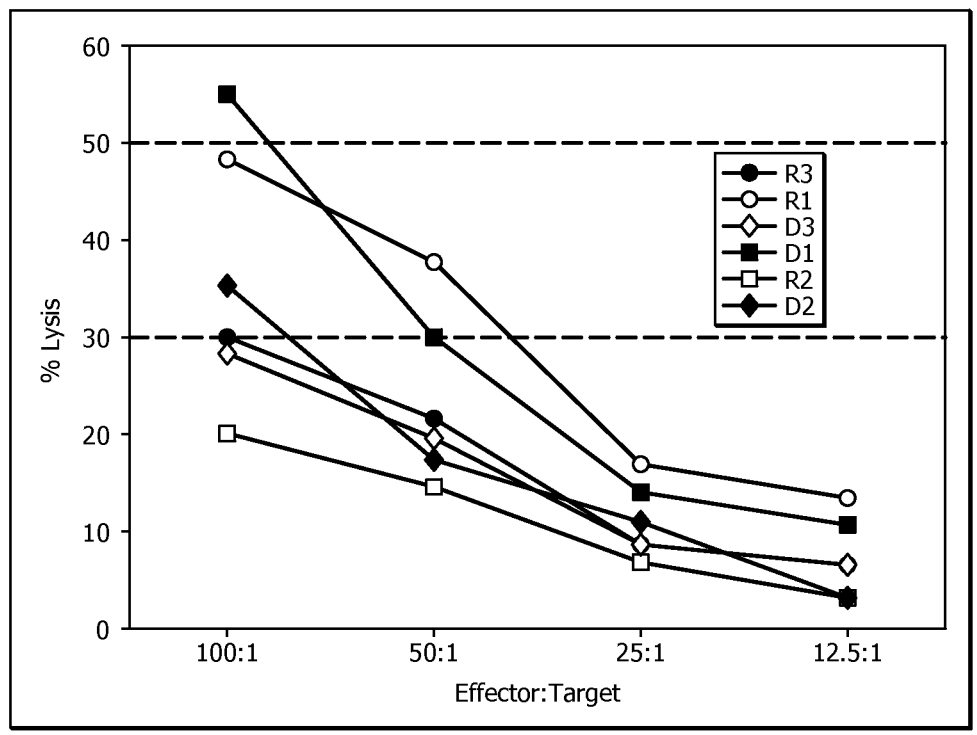
FIGS. 13 and 14 depict the results of the natural killer cell assay for the samples from Example 6.
Figure 14:
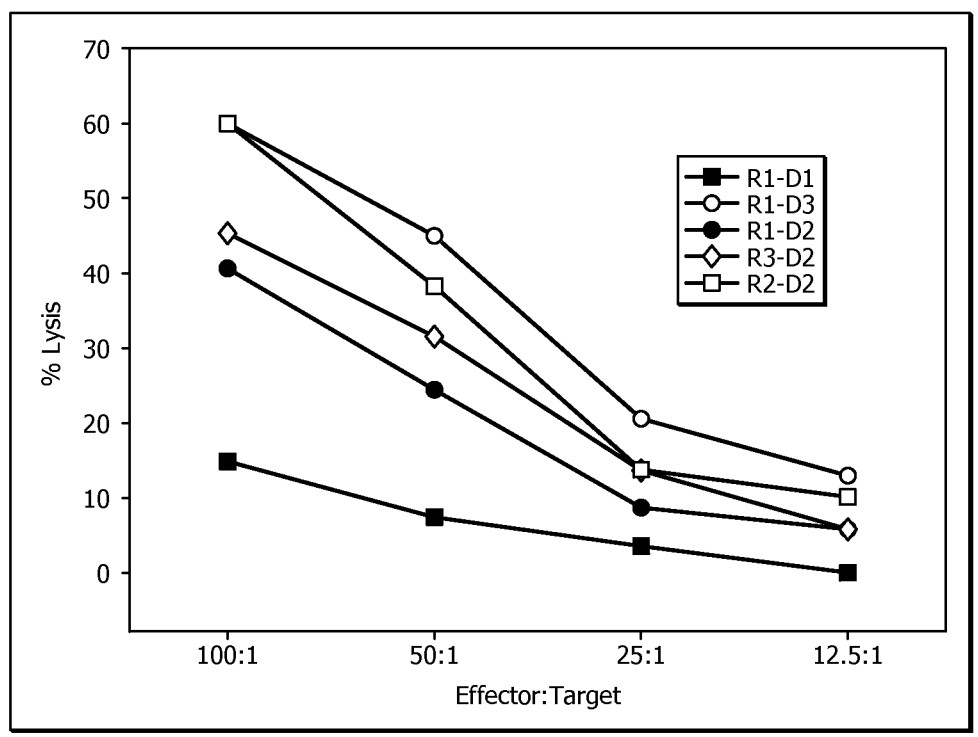

The innate immune function of the baseline donor cell samples and receiver cell samples were evaluated using a natural killer cell assay, FIG. 13. The assay was also performed on restored samples, FIG. 14. The restored cell samples are identified by the receiver cell sample-donor cell sample that were contacted, for example, receiver cell sample 3 and donor cell sample D2 are listed as R3-D2. The data demonstrate that the restored cell samples R1-D3, R1-D2, R3-D2, and R2-D2 maintained proper immune function while restored cell sample R1-D1 had decreased immune function. The data illustrate that for D2 and D3 the restored cell samples are characterized by an improvement in cellular immune function as quantified by natural killer cell cytotoxicity assay, as illustrated in FIGS. 13 and 14, and/or T-cell mitogen response assay.

Figure 15:
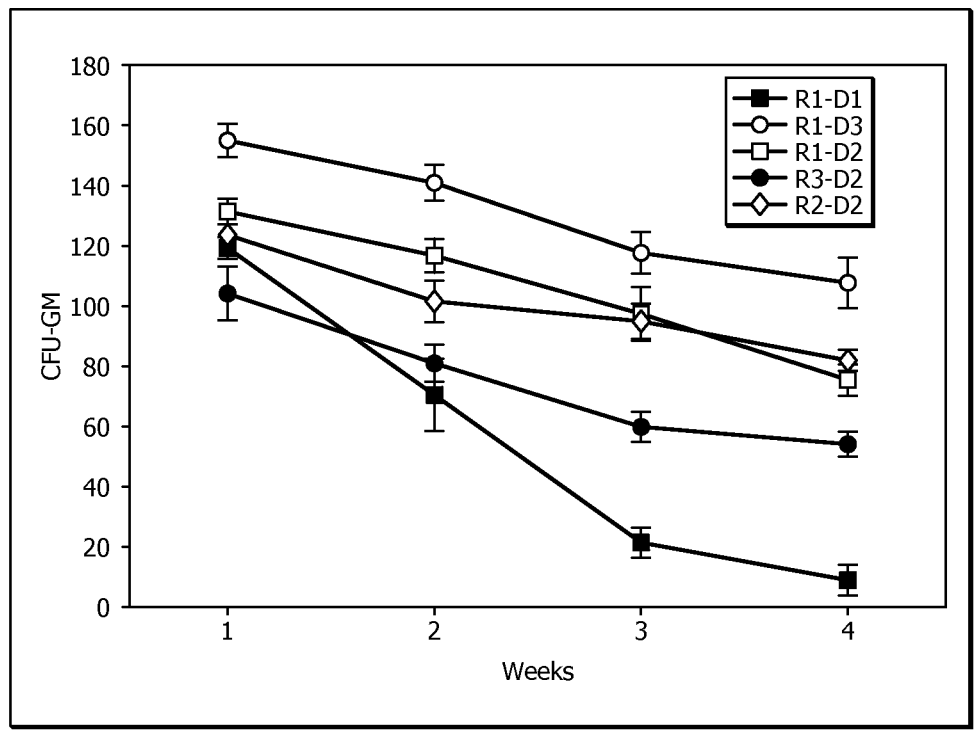
FIG. 15 depicts the results of the clonogenic assay for the samples from Example 6.

The hematopoietic function of the baseline donor cell samples and receiver cell samples were evaluated using a clonogenic assay, FIG. 15. The data demonstrate that the restored cell samples R1-D3, R1-D2, R3-D2, and R2-D2 maintained proper hematopoietic function while restored cell sample R1-D1 had decreased hematopoietic function. The data illustrate that the restored cell sample is characterized by an improvement in cellular hematopoietic function as quantified by hematopoietic stem cell clonogenic assay, as observed in FIG. 15.

Figure 16A:
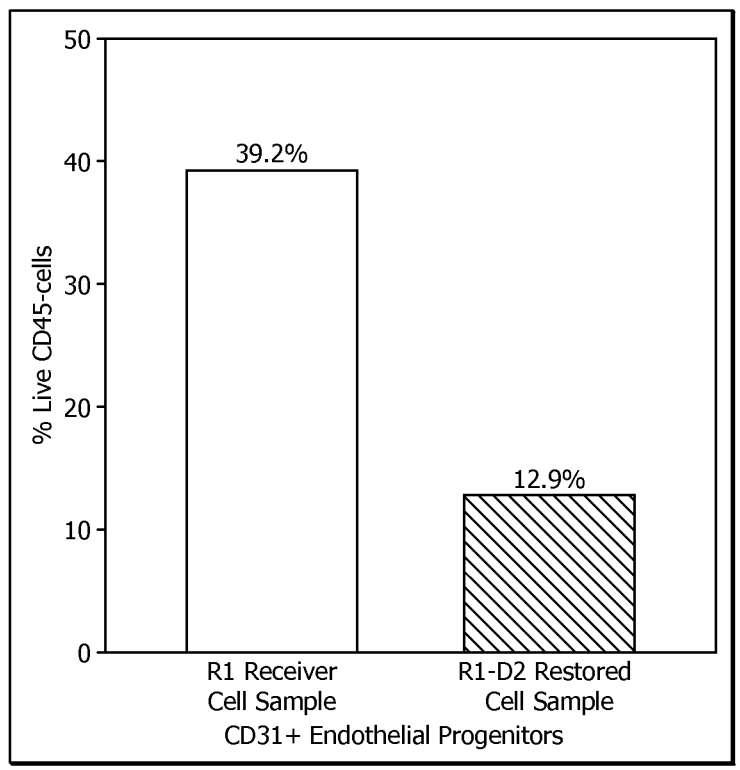
FIGS. 16A-D depict the results of a flow cytometry assay for the samples from Example 6.
Figure 16B:
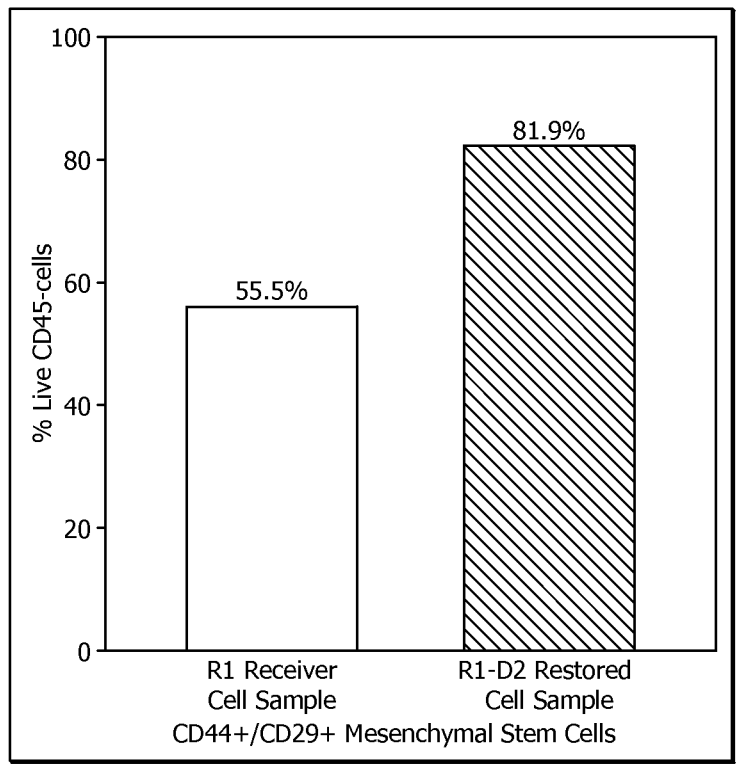
Figure 16C:
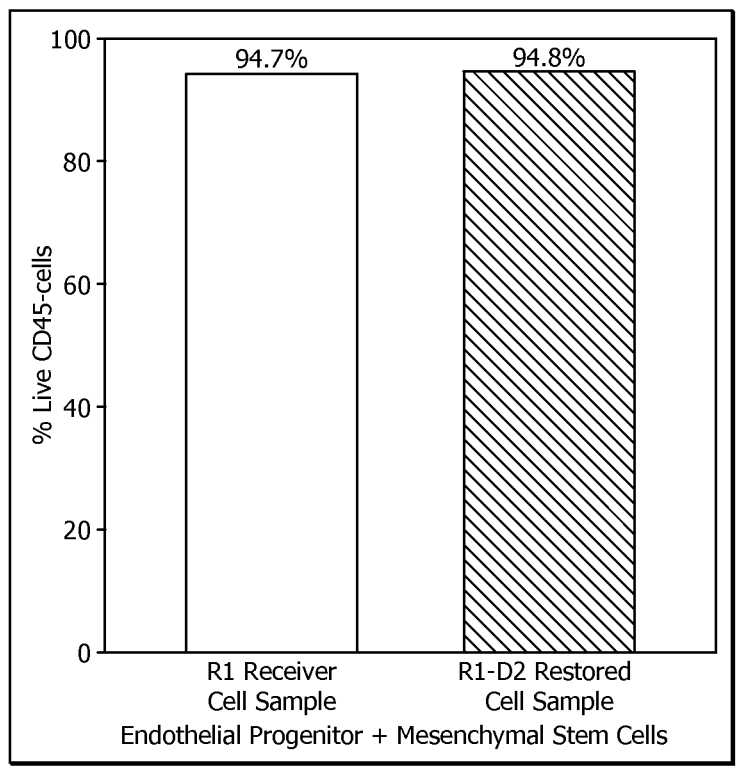
Figure 16D:
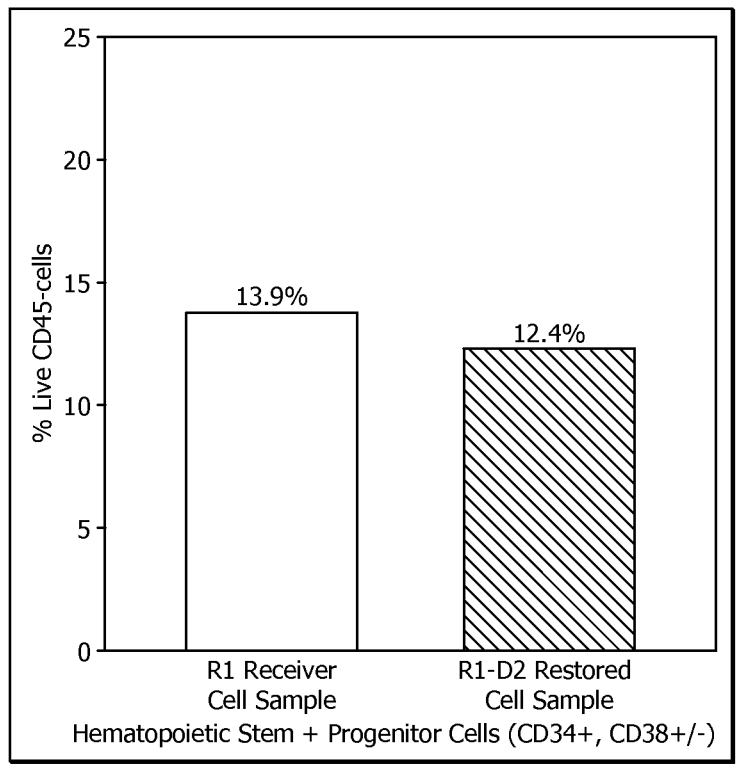

Cell population analyses were performed by flow cytometry to investigate whether the original distribution of cell types in the receiver cell sample, R1, was altered by the 4-week restoration process with donor cell sample D2. The results, shown in FIGS. 16A-16D, demonstrated that although there was some loss in the percentage of endothelial progenitor cells (FIG. 16A), there was an expansion of the mesenchymal stem cell compartment (FIG. 16B). As shown in FIG. 16C, a combination of the percentages of non-hematopoietic cells (i.e., from FIGS. 16A and B) indicated that the total percentages of these populations were maintained during the restoration process. Similarly, as shown in FIG. 16D, the percentages of hematopoietic stem and progenitor cells were insignificantly changed. These data demonstrate that the restored composition prepared by the methodologies disclosed herein is characterized by a lack of change in the percentage of hematopoietic stem cells, hematopoietic progenitor cells, mesenchymal stem cells and endothelial progenitor cells, herein termed the "stem cell pool", in receiver cells after cellular restoration compared to receiver samples at baseline, as observed in FIG. 16, by flow cytometry.

Example 7

The role of exosomes in cellular restoration was investigated. Exosomes were collected from cells that were cultured in exosomes-free media. The complete media containing sera were cleared of exosomes by overnight ultracentrifugation at 100,000 g and then stored at 40 C. Media were collected and then subjected to differential ultracentrifugation to isolate exosomes. The media was cleared of cells by centrifugation at 2,000 g for 20 min. The supernatant was transferred to a sterile tube for centrifugation at 10,000 g for 30 min to remove remaining cell debris and large vesicles. The supernatant was transferred to ultracentrifuge tubes and spun at 100,000 g for 80 min. The supernatant was disposed and the exosome pellet was washed with PBS. A final spin was done at 100,000 g for 80 min and the exosome pellet was either resuspended in 100 µl PBS for TEM or for the extraction of RNA. Exosome collection from smaller volumes was performed with the Total Exosome Isolation kit from Invitrogen. The isolation protocol followed manufacturer's guidelines. Collected exosomes washed once with PBS. Exosome samples were diluted in PBS to a final protein concentration of 100 µg/ml. In brief, 20 µl of exosome solution was placed on formavar carbon coated grids. The solution was wicked off the grid with filter paper and 20 µl of PTA (phosptungstaic acid) stain solution was then placed on the grid and wicked off with filter paper. The grid was scoped on a JEOL 1200EX electron microscope and digital images were obtained using an Advanced Microscopy Techniques (AMT camera) (Woburn, Mass.).

The following enumerated embodiments are provided as non-limiting examples.

A first embodiment which is a method comprising (i) obtaining a first cell sample from a first subject; (ii) obtaining a second cell sample from a second subject; (iii) culturing the first cell sample in the presence of at least a portion of a culture media of the second cell sample for a time period ranging from about 24 hours to about 6 weeks to produce a restoring composition; and (iv) contacting the restoring composition with the second cell sample for a period of time ranging from about 24 hours to about 6 weeks to produce a restored composition.

A second embodiment which is the method of the first embodiment further comprising immunophenotyping the first cell sample, the second cell sample, the restored composition, or combinations thereof.

A third embodiment which is the method of any of the first through second embodiments wherein the first subject, the second subject, or both are related by consanguinity.

A fourth embodiment which is the method of any of the first through third embodiments wherein the first subject and the second subject differ in chronological age by from about 5 years to about 75 years.

A fifth embodiment which is the method of any of the first through fourth embodiments wherein the second subject has a medical condition that is undiagnosed in the first subject.

A sixth embodiment which is the method of any of the first through fifth embodiments wherein the first subject, the second subject, or both have been administered a mobilizer prior to step (i).

A seventh embodiment which is the method of any of the first through sixth embodiments wherein the first cell sample and second cell sample comprise adult stem cells.

An eighth embodiment which is the method of any of the first through seventh embodiments wherein the first cell sample and second cell sample exclude stem cells that are embryonic in origin.

A ninth embodiment which is the method of any of the first through eighth embodiments wherein the first cell sample, the second cell sample, or both are obtained from a subject's peripheral blood.

A tenth embodiment which is the method of any of the first through ninth embodiments wherein the first cell sample, the second cell sample, or both are harvested directly from a subject's bone marrow.

An eleventh embodiment which is the method of any of the first through tenth embodiments wherein the first cell sample, the second cell sample, or both comprise non-hematopoietic cells, mesenchymal stem cells, endothelial progenitor cells, hematopoietic stem cells, primitive hematopoietic stem cells, hematopoietic progenitor cells, differentiated hematopoietic cells, T-lymphocytes, natural killer cells, or combinations thereof.

A twelfth embodiment which is the method of any of the first through twelfth embodiments wherein the first cell sample, the second cell sample, or both comprise non-senescent and senescent cells.

A thirteenth embodiment which is the method of the twelfth embodiment wherein the non-senescent cells are present in an amount of from about 90% to about 99% based on the total cell number.

A fourteenth embodiment which is the restoring composition of the first embodiment.

A fifteenth embodiment which a kit comprising the restoring composition of the first embodiment.

A sixteenth embodiment which is a method comprising administering to a subject an effect amount of the restoring composition of the first embodiment.

A seventeenth embodiment which is a pharmaceutical formulation comprising the restoring composition of the first embodiment and an active selected from the group consisting of antimicrobials, steroids, pain medications, anti-inflammatory agents, growth factors; cytokines, hormones, and combinations thereof.

An eighteenth embodiment which is an exosome/microvesicle isolated from the first embodiment.

A nineteenth embodiment which is a microvesicle isolated from the restoring composition of the first embodiment.

A twentieth embodiment which is a kit comprising a microvesicle isolated from the restoring composition of the first embodiment.

A twenty-first embodiment which is a kit comprising an exosome isolated from the restoring composition of the first embodiment.

A twenty-second embodiment which is a method comprising administering to a subject an effect amount of an exosome isolated from the restoring composition of the first embodiment.

A twenty-third embodiment which is a method comprising administering to a subject an effect amount of a microvesicle isolated from the restoring composition of the first embodiment.

A twenty-fourth embodiment which is a pharmaceutical formulation comprising an exosome isolated from the restoring composition of the first embodiment and an active selected from the group consisting of antimicrobials, steroids; pain medications, anti-inflammatory agents, growth factors, cytokines, hormones, and combinations thereof.

A twenty-fifth embodiment which is a pharmaceutical formulation comprising a microvesicle isolated from the restoring composition of the first embodiment and an active selected from the group consisting of antimicrobials, steroids; pain medications, anti-inflammatory agents, growth factors, cytokines, hormones, and combinations thereof.

A twenty-sixth embodiment which is a plurality of exosomes isolated from the restoring composition of the first embodiment.

A twenty-seventh embodiment which is a plurality of microvesicles isolated from the restoring composition of claim 1.

A twenty-eighth embodiment which is a cell free media prepared by filtration of the restoring composition of claim 1 wherein the cell free media comprise extracellular vesicles.

A twenty-ninth embodiment which is a method comprising contacting a receiver cell sample with a donor cell sample to produce a restored composition wherein the restored composition has an innate immune function as determined by a natural killer cell assay that is increased when compared to the innate immune function of the receiver cell sample and wherein the addition of mannumycin A to the donor cell sample prior to contact with the receiver cell sample inhibits the increase in innate immune function of the restored composition.

A thirtieth embodiment which is a pharmaceutical formulation comprising exosomes derived from mobilized stem cells, and one or more pharmaceutically acceptable carriers, adjuvants, or vehicles.

A thirty-first embodiment which is the formulation of the thirtieth embodiment further comprising an agent chosen from the group consisting of antimicrobials, steroids, pain medications, anti-inflammatory agents; growth factors, cytokines, hormones, and combinations thereof.

A thirty-second embodiment which is s kit comprising the formulation of the thirtieth embodiment.

A thirty-third embodiment which is a method comprising administering to a subject an effect amount of the formulation of the thirtieth embodiment.

A thirty-fourth embodiment which is a pharmaceutical formulation comprising a microvesicles derived from mobilized stem cells, and one or more pharmaceutically acceptable carriers, adjuvants, or vehicles.

A thirty-fifth embodiment which is the formulation of the thirty-fourth embodiment further comprising an agent chosen from the group consisting of antimicrobials, steroids, pain medications, anti-inflammatory agents; growth factors, cytokines, hormones, and combinations thereof.

A thirty-sixth embodiment which is a kit comprising the formulation of the thirty-fourth embodiment.

A thirty-seventh embodiment which is a method comprising administering to a subject an effect amount of the formulation of the thirty-fourth embodiment.

A thirty-eighth embodiment which is a pharmaceutical formulation comprising an exosome-derived and/or microvesicle derived molecule and one or more pharmaceutically acceptable carriers, adjuvants, or vehicles.

A thirty-ninth embodiment which is the formulation of the thirty-eighth embodiment wherein the exosome-derived and/or microvesicle derived molecule comprises proteins, cytokines, microvesicles, microvesicle complexes, microRNAs, large non-coding RNAs or combinations thereof.

A fortieth embodiment which is a kit comprising the formulation of the thirty-eighth embodiment.

A forty-first embodiment which is a method comprising administering to a subject an effect amount of the formulation of the thirty-eighth embodiment.

A forty-second embodiment which is a pharmaceutical formulation comprising a material selected from the group consisting of recombinant proteins, recombinant nucleic acids, synthetic metabolites, and synthetic lipids and one or more pharmaceutically acceptable carriers, adjuvants, or vehicles wherein the material can be derived from an exosome or microvesicle.

A forty-third embodiment which is the formulation of the forty-second embodiment further comprising an agent chosen from the group consisting of antimicrobials, steroids, pain medications, anti-inflammatory agents; growth factors, cytokines, hormones, and combinations thereof.

A forty-fourth embodiment which is a kit comprising the formulation of the forty-second embodiment.

A forty-fifth embodiment which is a method comprising administering to a subject an effect amount of the formulation of the forty-second embodiment.

A forty-sixth embodiment which is a method comprising (i) obtaining a first cell sample from a first subject; (ii) culturing the cell sample in for a time period ranging from about 24 hours to about 6 weeks to produce a restoring composition; and (iii) removing cells from the sample to produce a cell-free restoring composition.

A forty-seventh embodiment which is the method of the forty-sixth embodiment further comprising contacting the cell-free restoring composition with a second cell sample obtained from a second subject.

A forty-eighth embodiment which is the method of the forty-sixth embodiment wherein the first subject, the second subject, or both are related by consanguinity.

A forty-ninth embodiment which is the method of the forty-sixth embodiment wherein the first subject and the second subject differ in chronological age by from about 5 years to about 75 years.

While embodiments of the present disclosure have been shown and described, modifications thereof can be made by one skilled in the art without departing from the spirit and teachings of the disclosure. The embodiments described herein are exemplary only, and are not intended to be limiting. Many variations and modifications of the disclosure are possible and are within the scope of the invention. Use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, etc.

Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the preferred embodiments of the present invention. The discussion of a reference in the Background is not an admission that it is prior art to the present invention, especially any reference that may have a publication date after the priority date of this application. The disclosures of all patents, patent applications, and publications cited herein are hereby incorporated by reference, to the extent that they provide exemplary, procedural or other details supplementary to those set forth herein.

For the purpose of any U.S. national stage filing from this application, all publications and patents mentioned in this disclosure are incorporated herein by reference in their entireties, for the purpose of describing and disclosing the constructs and methodologies described in those publications, which might be used in connection with the methods of this disclosure. Any publications and patents discussed above and throughout the text are provided solely for their disclosure prior to the filing date of the present application. Nothing herein is to be construed as an admission that the inventors are not entitled to antedate such disclosure by virtue of prior invention.

Unless indicated otherwise, when a range of any type is disclosed or claimed it is intended to disclose or claim individually each possible number that such a range could reasonably encompass, including any sub-ranges encompassed therein. When describing a range of measurements every possible number that such a range could reasonably encompass can, for example, refer to values within the range with one significant digit more than is present in the end points of a range. Moreover, when a range of values is disclosed or claimed, which Applicants intent to reflect individually each possible number that such a range could reasonably encompass, Applicants also intend for the disclosure of a range to reflect, and be interchangeable with, disclosing any and all sub-ranges and combinations of sub-ranges encompassed therein. Accordingly, Applicants reserve the right to proviso out or exclude any individual members of any such group, including any sub-ranges or combinations of sub-ranges within the group, if for any reason Applicants choose to claim less than the full measure of the disclosure.

The invention claimed is:

1. A cell-free pharmaceutical formulation comprising:
a therapeutically effective amount of exosomes, the exosomes being harvested from a heterogeneous cell population that is collected from blood from a donor who has been treated with filagrastim as a mobilizing agent, the heterogeneous cell population comprising hematopoietic cells, hematopoietic stem cell, hematopoietic progenitor cells, T cells, and natural killer cells; and
a synthetic antibiotic;
wherein the heterogeneous cell population is collected from the donor using apheresis;
wherein the exosomes are harvested from the heterogeneous cell population after exposing the heterogeneous cell population to culture conditions that promote the secretion of exosomes;

wherein the culture conditions comprise exosomes-free media; and wherein the therapeutically effective amount of exosomes is an amount sufficient to increase telomere length.

2. The pharmaceutical formulation of claim 1, further comprising one or more pharmaceutically acceptable carriers, adjuvants, or vehicles.

3. The formulation of claim 1 further comprising one or more surfactants, thickening agents, antioxidants, viscosity stabilizers, buffers, preservatives, vitamins, antibiotics, or a combination thereof.

4. The formulation of claim 1 wherein the formulation comprises phosphate buffered saline.

5. The formulation of claim 1, further comprising a vitamin.

* * * * *

UNITED STATES PATENT AND TRADEMARK OFFICE
CERTIFICATE OF CORRECTION

| | | |
|---|---|---|
| PATENT NO. | : 10,772,911 B2 | Page 1 of 3 |
| APPLICATION NO. | : 15/128660 | |
| DATED | : September 15, 2020 | |
| INVENTOR(S) | : Steven John Greco et al. | |

It is certified that error appears in the above-identified patent and that said Letters Patent is hereby corrected as shown below:

On the Title Page

Column 1, Item (60), Line 1, under Related U.S. Application Data, delete "61/696,694," and insert --61/969,694,--.

On Page 2, Column 2, Item (56), Line 4, under Other Publications, delete "Friontiers" and insert --Frontiers--.

On Page 2, Column 2, Item (56), Line 48, under Other Publications, delete "vol." and insert --No.--.

On Page 2, Column 2, Item (56), Line 54, under Other Publications, delete "vol." and insert --, No.--.

On Page 3, Column 2, Item (56), Line 38, under Other Publications, delete "Rjuvenation," and insert --Rejuvenation,--.

On Page 4, Column 1, Item (56), Line 3, under Other Publications, delete "FASB" and insert --FASEB--.

On Page 4, Column 1, Item (56), Line 5, under Other Publications, delete "Stimulation" and insert --Stimulating--.

On Page 4, Column 1, Item (56), Line 8, under Other Publications, delete "Cire" and insert --Circ.--.

On Page 4, Column 2, Item (56), Line 21, under Other Publications, delete "calls" and insert --cells--.

In the Specification

In Column 11, Line 3, delete "may" and insert --may be--.

In Column 11, Line 10, delete "teleomere" and insert --telomere--.

Signed and Sealed this
First Day of December, 2020

Andrei Iancu
*Director of the United States Patent and Trademark Office*

CERTIFICATE OF CORRECTION (continued)
U.S. Pat. No. 10,772,911 B2

In Columns 11-12, Line 37 (Approx.), delete "MCP" and insert --MIP--.

In Columns 11-12, Line 38 (Approx.), delete "(MIP3A)" and insert --(MIP-3α)--.

In Column 14, Line 33, delete "the a" and insert --the--.

In Column 17, Line 16, delete "Autogphagy" and insert --Autophagy--.

In Column 18, Line 14 (Approx.), delete "mannumycin" and insert --manumycin--.

In Column 18, Lines 60-61, delete "adminstration, intraaterial" and insert --administration, intraarterial--.

In Column 19, Line 48, delete "disulfuram" and insert --disulfiram--.

In Column 19, Line 48, delete "disulfuram-" and insert --disulfiram- --.

In Column 20, Lines 38-39, delete "Lomoxicam;" and insert --Lornoxicam;--.

In Column 20, Line 57, delete "Propirarn" and insert --Propiram--.

In Column 21, Line 3, delete "Zucapsaicin., Aflyzosin" and insert --Zucapsaicin; Alfuzosin--.

In Column 21, Line 17, delete "Eeadotril;" and insert --Ecadotril;--.

In Column 21, Line 49, delete "Tierynafen;" and insert --Ticrynafen;--.

In Column 22, Line 14, delete "Momiflumate;" and insert --Morniflumate;--.

In Column 22, Line 51, delete "adminstration, intraaterial" and insert --administration, intraarterial--.

In Column 26, Line 16, delete "(mtDNA," and insert --(mtDNA),--.

In Column 27, Lines 64-65, delete "(filagrastim)." and insert --(filgrastim).--.

In Column 30, Line 55, delete "immunosorbant" and insert --immunosorbent--.

In Column 31, Line 17, delete "farnesytransferase" and insert --farnesyltransferase--.

In Column 31, Line 18, delete "Mannumycin" and insert --Manumycin--.

In Column 32, Line 48, delete "formavar" and insert --formvar--.

In Column 32, Line 50, delete "(phosptungstaic" and insert --(phosphotungstic--.

In Column 34, Lines 43-44, delete "mannumycin" and insert --manumycin--.

CERTIFICATE OF CORRECTION (continued)
U.S. Pat. No. 10,772,911 B2

In the Claims

In Column 36, Line 56, Claim 1, delete "filagrastim" and insert --filgrastim--.